United States Patent [19]
Breault

[11] Patent Number: 6,100,258
[45] Date of Patent: Aug. 8, 2000

[54] AROMATIC AMINE COMPOUNDS THAT ANTAGONIZE THE PAIN ENHANCING EFFECTS OF PROSTAGLANDINS

[75] Inventor: Gloria Anne Breault, Macclesfield, United Kingdom

[73] Assignee: Zeneca Limited, United Kingdom

[21] Appl. No.: 08/973,915

[22] PCT Filed: Jun. 17, 1996

[86] PCT No.: PCT/GB96/01443

§ 371 Date: Dec. 16, 1997

§ 102(e) Date: Dec. 16, 1997

[87] PCT Pub. No.: WO97/00864

PCT Pub. Date: Jan. 9, 1997

[30] Foreign Application Priority Data

Jun. 20, 1995 [GB] United Kingdom .................. 9512475
Jan. 25, 1996 [GB] United Kingdom .................. 9601465

[51] Int. Cl.$^7$ ..................... A61K 31/5377; A61K 31/50; C07D 237/24; C07D 403/04

[52] U.S. Cl. ..................... 514/236.5; 514/252; 514/340; 514/354; 514/355; 514/356; 514/576; 514/620; 544/114; 544/224; 544/238; 546/322; 546/323; 546/326; 546/268.4; 562/451; 564/165

[58] Field of Search ............................. 514/252, 236.5; 544/224, 238, 114

[56] References Cited

U.S. PATENT DOCUMENTS

| | | | |
|---|---|---|---|
| 3,632,760 | 1/1972 | Shen et al. | 424/230 |
| 3,657,430 | 4/1972 | Shen et al. | 424/230 |
| 4,152,452 | 5/1979 | Doulgas et al. | 424/304 |
| 4,206,145 | 6/1980 | Hindley et al. | 560/19 |
| 4,277,496 | 7/1981 | Los | 424/308 |
| 4,350,822 | 9/1982 | Albright et al. | 560/45 |
| 4,362,892 | 12/1982 | Hindley et al. | 564/374 |
| 4,578,390 | 3/1986 | Jensen et al. | 514/255 |
| 4,590,199 | 5/1986 | Coker et al. | 514/343 |
| 4,631,287 | 12/1986 | Chakraborty et al. | 514/247 |
| 4,725,619 | 2/1988 | Chakraborty et al. | 514/442 |
| 4,728,668 | 3/1988 | Chakraborty et al. | 514/464 |
| 4,839,369 | 6/1989 | Youssefyeh et al. | 514/314 |
| 4,937,373 | 6/1990 | Carson et al. | 560/56 |
| 5,087,743 | 2/1992 | Jansen et al. | 562/466 |
| 5,105,017 | 4/1992 | Diuard | 568/64 |
| 5,189,033 | 2/1993 | Tucker | 514/211 |
| 5,210,206 | 5/1993 | Morton et al. | 548/238 |
| 5,250,548 | 10/1993 | Winn et al. | 514/340 |
| 5,284,954 | 2/1994 | Wittenberger et al. | 546/276 |
| 5,317,101 | 5/1994 | Tucker et al. | 540/488 |
| 5,324,743 | 6/1994 | Dillard et al. | 514/456 |
| 5,393,768 | 2/1995 | Dillard et al. | 514/381 |
| 5,409,930 | 4/1995 | Spada et al. | 514/248 |
| 5,420,270 | 5/1995 | Chandrakumar et al. | 540/488 |
| 5,441,950 | 8/1995 | Collins et al. | 540/481 |
| 5,480,883 | 1/1996 | Spada et al. | 514/249 |
| 5,530,157 | 6/1996 | Mewshaw et al. | 562/490 |
| 5,811,459 | 9/1998 | Breault et al. | 514/555 |
| 5,834,468 | 11/1998 | Breault et al. | 514/247 |
| 5,843,942 | 12/1998 | Breault et al. | 514/247 |

FOREIGN PATENT DOCUMENTS

| | | |
|---|---|---|
| 2111035 | 6/1994 | Canada. |
| 0000816 | 2/1979 | European Pat. Off. . |
| 0094065 | 11/1983 | European Pat. Off. . |
| 0193822 | 9/1986 | European Pat. Off. . |
| 0218077 | 4/1987 | European Pat. Off. . |
| 0475206 | 3/1992 | European Pat. Off. . |
| 0752421 | 1/1997 | European Pat. Off. . |

(List continued on next page.)

OTHER PUBLICATIONS

Derwent Abstract of DE 1,543,519 (Abstract No. 71–26731S/16), 1971.

Derwent Abstract of WO 93/23364 (Abstract No. 93–386430/48), 1993.

Chem. Abstracts, vol. 91, No. 27, 1979, abstract 56831t, p. 691.

Chem. Abstracts, vol. 101, 1984, abstract 63594w.

Chem. Abstracts, vol. 102, 1985, abstract 1871w.

Albright et al., J. Med. Chem. 1983, 26, 1378–1393, Potential Antiatherosclerotic Agents, 2,' (Aralkylamino)–and (Alkylamino) benzoic Acid Analogues of Cetaben.

Brown et al., J. Med. Chem., 1989, 32, 807–825, Hydroxyacetophenone–Derived Antagonists of the Peptidolekotrienes.

Mazumder et al., Biochemistry, 1995, 34, pp. 15111–15122, Effects of Tyrphostins, Protein kinase Inhibitors, on Human Immunodeficiency Virus Type 1 Integrase.

Chen et al, J. Med. Chem., 1993, 36, 4094–4098, Synthesis and Structure–Activity Studies of a Series of [(Hydroxybenzyl)amino]Salicylates as Inhibitors of EGF Receptor–Associated Tyrosine Kinase Activity.

Hsu et al., J. of Biological Chemistry, 1991, Bol. 266, No. 31, Issue of Nov. 5, pp. 21105–21112, Kinetic Analysis of the Inhibition of the Epidermal Growth Factor Receptor Tyrosine Kinase by Lavendustin–A and its Analogue.

Iskander et al., Eur J. Med Chem, 1991, 26, 129–136, Transition–state analogues as inhibotors for GABA–aminotransferase.

Walker et al., J. Med. Chem., 1966, 9, 624–630, Synthesis of Varied Heterocyclic and Substituted Aryl Alkyl Secondary Amines, Related Schiff, Bases, and Amides.

*Primary Examiner*—Emily Bernhardt
*Attorney, Agent, or Firm*—Kenneth F. Mitchell

[57] ABSTRACT

Compounds antagonistic of the pain enhancing effects of prostaglandins are disclosed. The compounds comprise an optionally-substituted A ring with a —CH($R^3$)N($R^2$)B—$R^1$ and —OD groups positioned in a 1,2 relationship to one another on ring carbon atoms. The 3-position ring-atom is not substituted. B is also an optionally-substituted ring and the group $R^1$ is positioned on B in a 1,3 or 1,4 relationship with the —CH($R^3$)N($R^2$)— linking group. $R^1$, $R^2$ and $R^3$ and D can be a number of different organic or halogen moieties. N-oxides of —N$R^2$ and S-oxides of sulphur containing rings are disclosed as are processes for the preparation of the compounds, intermediates in their preparation, pharmaceutical compositions containing them, and their use as therapeutic agents.

11 Claims, No Drawings

FOREIGN PATENT DOCUMENTS

| | | | | | |
|---|---|---|---|---|---|
| 1393727 | 5/1975 | United Kingdom . | WO 96/03380 | 2/1996 | WIPO . |
| 1560281 | 2/1980 | United Kingdom . | WO 96/06822 | 3/1996 | WIPO . |
| 2041363 | 9/1980 | United Kingdom . | WO 96/11902 | 4/1996 | WIPO . |
| | | | WO 97/00863 | 1/1997 | WIPO . |
| | | | WO 97/00864 | 1/1997 | WIPO . |

AROMATIC AMINE COMPOUNDS THAT ANTAGONIZE THE PAIN ENHANCING EFFECTS OF PROSTAGLANDINS

This invention relates to novel, aromatic compounds and pharmaceutically-acceptable salts thereof which possess useful pharmacological properties. More particularly the compounds of the invention are antagonists of the pain enhancing effects of E-type prostaglandins. The invention also relates to processes for the manufacture of the aromatic compounds and pharmaceutically-acceptable salts thereof; to novel pharmaceutical compositions containing them; and to use of the compounds in pain relief.

The compounds of the invention are useful in the treatment of mild to moderate pain such as the pain associated with joint conditions (such as rheumatoid arthritis and osteoarthritis), postoperative pain, post-partum pain, the pain associated with dental conditions (such as dental caries and gingivitis), the pain associated with burns (including sunburn), the treatment of bone disorders (such as osteoporosis, hypercalcaemia of malignancy and Paget's disease), the pain associated with sports injuries and sprains and all other painful conditions in which E-type prostaglandins wholly or in part play a pathophysiological role.

Non-steroidal anti-inflammatory drugs (NSAIDS) and opiates are the main classes of drugs in mild to moderate pain relief. However both classes possess undesirable side effects. NSAIDS are known to cause gastrointestinal irritation and opiates are known to be addictive.

We have now found a class of compounds structurally different to NSAIDS and opiates, and useful in relief of mild to moderate pain.

The compounds of the invention may also possess anti-inflammatory, anti-pyretic and anti-diarrhoeal properties and be effective in other conditions in which prostaglandin $E_2$ ($PGE_2$) wholly or in part plays a pathophysiological role.

According to the invention there is provided a compound of the formula I;

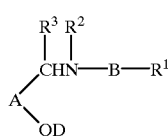

(I)

wherein:

A is an optionally substituted: phenyl, naphthyl, pyridyl, pyrazinyl, pyridazinyl, pyrimidyl, thienyl, thiazolyl, oxazolyl or thiadiazolyl having at least two adjacent ring carbon atoms; provided that the —CH($R^3$)N($R^2$)B—$R^1$ and —OD groups are positioned in a 1,2 relationship to one another on ring carbon atoms and the ring atom positioned ortho to the —OD linking group (and therefore in the 3-position relative to the —CHR$^3$NR$^2$-linking group) is not substituted;

B is an optionally substituted: phenyl, pyridyl, thiazolyl, oxazolyl, thienyl, thiadiazolyl, imidazolyl, pyrazinyl, pyridazinyl or pyrimidyl;

$R^1$ is positioned on ring B in a 1,3 or 1,4 relationship with the —CH($R^3$)N($R^2$)-linking group and is carboxy, carboxy$C_{1-3}$alkyl, tetrazolyl, tetrazolyl$C_{1-3}$alkyl, tetronic acid, hydroxamic acid, sulphonic acid, or $R^1$ is of the formula —CONR$^a$R$^{a1}$ wherein R$^a$ is hydrogen or $C_{1-6}$alkyl and R$^{a1}$ is hydrogen, $C_{1-6}$alkyl (optionally substituted by halo, amino, $C_{1-4}$alkylamino, di-$C_{1-4}$alkylamino, hydroxy, nitro, cyano, trifluoromethyl, $C_{1-4}$alkoxy or $C_{1-4}$alkoxycarbonyl), $C_{2-6}$alkenyl (provided the double bond in not in the 1-position), $C_{2-6}$alkynyl (provided the triple bond is not in the 1-position), carboxyphenyl, 5- or 6-membered heterocyclyl$C_{1-3}$alkyl, 5- or 6-membered heteroaryl$C_{1-3}$alkyl, 5- or 6-membered heterocyclyl, or 5- or 6-membered heteroaryl, or R$^a$ and R$^{a1}$ together with the amide nitrogen to which they are attached (NR$^a$R$^{a1}$) form an amino acid residue or ester thereof or $R^1$ is of the formula —CONHSO$_2$R$^b$ wherein R$^b$ is $C_{1-6}$alkyl (optionally substituted by halo, hydroxy, nitro, cyano, amino, $C_{1-4}$alkylamino, di-$C_{1-6}$alkylamino, trifluoromethyl, $C_{1-4}$alkoxy or $C_{1-4}$alkoxycarbonyl), $C_{2-6}$alkenyl (provided the double bond is not in the 1-position), $C_{2-6}$alkynyl (provided the triple bond is not in the 1-position), 5- or 6-membered heterocyclyl$C_{1-3}$alkyl, 5- or 6-membered heteroaryl$C_{1-3}$alkyl phenyl$C_{1-3}$alkyl, 5- or 6-membered heterocyclyl, 5- or 6-membered heteroaryl or phenyl; wherein any heterocyclyl or heteroaryl group in R$^{a1}$ is optionally substituted by halo, hydroxy, nitro, cyano, trifluoromethyl, $C_{1-4}$alkoxy or $C_{1-4}$alkoxycarbonyl and any phenyl, heterocyclyl or heteroaryl group in R$^b$ is optionally substituted by halo, trifluoromethyl, nitro, hydroxy, amino, cyano, $C_{1-6}$alkoxy, S(O)p$C_{1-6}$alkyl (p is 0, 1 or 2), $C_{1-6}$alkyl carbamoyl, $C_{1-4}$alkylcarbamoyl, di($C_{1-4}$alkyl)carbamoyl, $C_{2-6}$alkenyl, $C_{2-6}$alkynyl $C_{1-4}$alkoxycarbonylamino, $C_{1-4}$alkanoylamino, $C_{1-4}$alkanoyl(N-$C_{1-4}$alkyl)amino, $C_{1-4}$alkanesulphonamido, benzenesulphonamido, aminosulphonyl, $C_{1-4}$alkylaminosulphonyl, di($C_{1-4}$alkyl)aminosulphonyl, $C_{1-4}$alkoxycarbonyl, $C_{1-4}$alkanoyloxy,$C_{1-6}$alkanoyl, formyl$C_{1-4}$alkyl, hydroxyimino$C_{1-6}$alkyl, $C_{1-4}$alkoxyimino$C_{1-6}$alkyl or $C_{1-6}$alkylcarbamoylamino; or $R^1$ is of the formula —SO$_2$N(R$^c$)R$^{c1}$ wherein R$^c$ is hydrogen or $C_{1-4}$alkyl and R$^{c1}$ is hydrogen or $C_{1-4}$alkyl; or $R^1$ is of the formula (IA), (IB) or (IC):

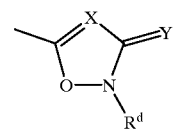

(IA)

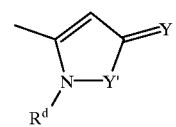

(IB)

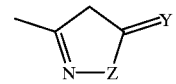

(IC)

wherein X is CH or nitrogen, Y is oxygen or sulphur, Y' is oxygen or NR$^d$ and Z is CH$_2$, NR$^d$ or oxygen provided that there is no more than one ring oxygen and there are at least two ring heteroatoms and wherein R$^d$ is hydrogen or $C_{1-4}$alkyl;

$R^2$ is hydrogen, $C_{1-6}$alkyl, optionally substituted by hydroxy, cyano or trifluoromethyl, $C_{2-6}$alkenyl (provided the double bond is not in the 1-position), $C_{2-6}$alkynyl (provided the triple bond is not in the 1-position), phenyl$C_{1-3}$alkyl or pyridyl$C_{1-3}$alkyl;

$R^3$ is hydrogen, methyl or ethyl;

D is hydrogen, an optionally substituted 5–7 membered carbocyclic ring containing one double bond, $C_{1-3}$alkyl substituted by an optionally substituted 5–7 membered carbocyclic ring containing one double bond or D is of the formula —$(CH_2)nCH(R^4)C(R^5)=C(R^6)R^7$ wherein:

$R^4$ is hydrogen, methyl or ethyl;

$R^5$ is hydrogen, methyl, bromo, chloro, fluoro or trifluoromethyl;

$R^6$ is hydrogen, $C_{1-4}$alkyl, bromo, chloro, fluoro or trifluoromethyl;

$R^7$ is hydrogen, $C_{1-4}$alkyl, bromo, chloro, fluoro or trifluoromethyl;

n is 0 or 1;

and N-oxides of —$NR^2$ where chemically possible; and S-oxides of sulphur containing rings where chemically possible; and pharmaceutically acceptable salts and in vivo hydrolysable esters and amides thereof; excluding 4-[5-carboxy-2-hydroxybenzylamino] benzoic acid, 4-[2,5-dihydroxybenzylamino]benzoic acid, 5-[2-hydroxybenzylamino]-2-hydroxybenzoic acid, 3-[2,5-dihydroxybenzylamino]benzoic acid, 4-[2,5-dihydroxybenzylamino]benzenecarboxamide, 3-[2-hydroxybenzylamino]benzoic acid, 4-[2,5-dihydroxybenzylamino]-2-hydroxybenzoic acid, 4-[2-hydroxybenzylamino]-2-hydroxybenzoic acid and 4-[2-hydroxybenzylamino]benzoic acid.

A 5- or 6-membered heteroaryl ring system is a monocyclic aryl ring system having 5 or 6 ring atoms wherein 1, 2 or 3 ring atoms are selected from nitrogen, oxygen and sulphur.

A 5- or 6-membered saturated or partially saturated heterocyclic ring is a ring system having 5 or 6 ring atoms wherein 1, 2 or 3 of the ring atoms are selected from nitrogen, oxygen and sulphur.

A 5–7 membered carbocyclic ring containing one double bond is monocyclic and contains only one double bond.

Particular 5- or 6-membered monocyclic heteroaryl rings include pyrrolyl, imidazolyl, pyrazolyl, isothiazolyl, isoxazolyl, pyridyl, pyrazinyl, pyrimidinyl, pyridazinyl, thiazolyl, thiadiazolyl, thienyl, furyl and oxazolyl.

Particular 5- or 6-membered saturated or partially saturated heterocyclic ring ring systems include pyrrolidinyl, pyrrolinyl, imidazolidinyl, pyrazolidinyl, piperidyl, piperazinyl and morpholinyl.

Particular 5–7 membered carbocyclic ring systems containing one double bond include cyclohexen-3-yl, cyclopenten-2-yl and cyclopenten-3-yl.

Particular substituents for ring carbon atoms in A and heteroaryl or heterocyclyl rings include halo, trifluoromethyl, nitro, hydroxy, amino, $C_{1-4}$alkylamino, di$C_{1-4}$alkylamino, cyano, $C_{1-6}$alkoxy, $S(O)_pC_{1-6}$alkyl (p is 0, 1 or 2), $C_{1-6}$alkyl (optionally substituted by hydroxy, amino, halo, nitro or cyano), $S(O)_pCF_3$ (p=0, 1 or 2), carbamoyl, $C_{1-4}$alkylcarbamoyl, di($C_{1-4}$alkyl)carbamoyl, $C_{2-6}$alkenyl, $C_{2-6}$alkynyl, $C_{1-4}$alkoxycarbonylamino, $C_{1-4}$alkanoylamino, $C_{1-4}$alkanoyl(N-$C_{1-4}$alkyl)amino, $C_{1-4}$alkanesulphonamido, benzenesulphonamido, aminosulphonyl, $C_{1-4}$alkylaminosulphonyl, di($C_{1-4}$alkyl)aminosulphonyl, $C_{1-4}$alkoxycarbonyl, $C_{1-4}$alkanoyloxy, $C_{1-6}$alkanoyl, formyl$C_{1-4}$alkyl, trifluoro$C_{1-3}$alkylsulphonyl, hydroxyimino$C_{1-6}$alkyl, $C_{1-4}$alkoxyimino$C_{1-6}$alkyl and $C_{1-6}$alkylcarbamoylamino.

Where a ring nitrogen atom in A can be substituted without becoming quaternised, it is unsubstituted or substituted by $C_{1-4}$alkyl.

Particular substituents for ring carbon atoms in B include halo, trifluoromethyl, nitro, hydroxy, $C_{1-6}$alkoxy, $C_{1-6}$alkyl, amino, $C_{1-4}$alkylamino, di($C_{1-4}$alkyl)amino, cyano, —$S(O)pC_{1-6}$alkyl (p is 0, 1 or 2), carbamoyl, $C_{1-4}$alkylcarbamoyl and di($C_{1-4}$alkyl)carbamoyl.

Where a ring nitrogen atom in B can be substituted without becoming quaternised, it is unsubstituted or substituted by $C_{1-4}$alkyl.

Particular substituents for the 5–7 membered carbocyclic ring containing one double bond (D) include $C_{1-4}$alkyl, $C_{2-4}$alkenyl, $C_{2-4}$alkynyl, halo, hydroxy, amino, $C_{1-4}$alkylamino, di-($C_{1-4}$alkyl)amino, cyano, trifluoromethyl, oxo, $C_{1-4}$alkanoyl, carboxy and carbamoyl.

The term alkyl when used herein includes straight chain and branched chain substituents for example methyl, ethyl, n-propyl, isopropyl, n-butyl and isobutyl and functional groups on alkyl chains may be anywhere on the chain, for example hydroxyimino$C_{1-6}$alkyl includes 1-(hydroxyimino) propyl and 2-(hydroxyimino)propyl.

Amino acid residues formed from $R^a$ and $R^{a1}$ together with the nitrogen to which they are attached include residues (—NHCH(R)COOH) derived from naturally-occurring and non-naturally-occurring amino acids. Examples of, suitable amino acids include glycine, alanine, serine, threonine, phenylalanine, glutamic acid, tyrosine, lysine and dimethylglycine.

Suitable ring systems of the formula (IA), (IB) or (IC) include 5-oxo-4,5-dihydro-1,2,4-oxadiazol-3-yl, 3-oxo-2,3-dihydro-1,2,4-oxadiazol-5-yl, 3-thioxo-2,3-dihydro-1,2,4-oxadiazol-5-yl, 5-oxo-4,5-dihydro-1,3,4-oxadiazol-2-yl, 5-oxo-4,5-dihydro-1,2,4-triazol-3-yl, 5-thioxo-4,5-dihydro-1,3,4-oxadiazol-2-yl, 1,3,4-oxadiazol-2-yl, 3-hydroxy-2-methylpyrazol-5-yl, 3-oxo-2,3-dihydroisoxazol-5-yl, 5-oxo-1,5-dihydroisoxazol-3-yl and 5-oxo-2,3-dihydropyrazol-3-yl.

Examples of $C_{1-6}$alkoxycarbonyl are methoxycarbonyl, ethoxycarbonyl and t-butoxycarbonyl; examples of carboxy$C_{1-3}$alkyl are carboxymethyl, 2-carboxyethyl, 1-carboxyethyl and 3-carboxypropyl; examples of $C_{1-6}$alkoxycarbonyl$C_{1-3}$alkyl are methoxycarbonylmethyl, ethoxycarbonylmethyl and methoxycarbonylethyl; examples of tetrazolyl$C_{1-3}$alkyl are tetrazolylmethyl and 2-tetrazolylethyl; examples of $C_{1-4}$alkoxy are methoxy, ethoxy, propoxy and isopropoxy; examples of $C_{2-6}$alkenyl are vinyl and allyl; examples of $C_{2-6}$alkynyl are ethynyl and propynyl; examples of $C_{1-4}$alkanoyl are formyl, acetyl, propionyl and butyryl; examples of halo are fluoro, chloro, bromo and iodo; examples of $C_{1-4}$alkylamino are methylamino, ethyl amino, propylamino and isopropylamino; examples of di($C_{1-4}$alkyl)amino are dimethylamino, diethylamino and ethylmethylamino; examples of —$S(O)_pC_{1-4}$alkyl are methylthio, methylsulphinyl and methylsulphonyl; examples of $C_{1-4}$alkylcarbamoyl are methylcarbamoyl and ethylcarbamoyl; examples of di($C_{1-4}$alkyl)carbamoyl are dimethylcarbamoyl, diethylcarbamoyl and ethylmethylcarbamoyl; examples of $C_{1-6}$alkyl are methyl, ethyl, propyl and isopropyl; examples of $C_{1-4}$alkoxycarbonylamino are methoxycarbonylamino and ethoxycarbonylamino; examples of $C_{1-4}$alkanoylamino are acetamido and propionamido; examples of $C_{1-4}$alkanoyl(N-$C_{1-4}$alkyl)amino are N-methylacetamido and N-methylpropionamido; examples of $C_{1-4}$alkanesulphonamido are methanesulphonamido and ethanesulphonamido; examples of $C_{1-4}$alkylaminosulphonyl are methylaminosulphonyl and ethylaminosulphonyl; examples of di($C_{1-4}$alkyl)aminosulphonyl are dimethylaminosulphonyl diethylaminosulphonyl and ethylmethylamino-sulphonyl; examples of $C_{1-4}$alkanoyloxy are acetyloxy and propionyloxy; examples of formyl$C_{1-4}$alkyl are formylmethyl and 2-formylethyl; examples of hydroxyimino$C_{1-6}$alkyl are hydroxyiminomethyl and 2-(hydroxyimino)ethyl; and examples of $C_{1-4}$alkoxyimino$C_{1-6}$alkyl are methoxyiminomethyl, ethoxyiminomethyl and 2-(methoxyimino)ethyl.

It will be understood that when formula I compounds contain a chiral centre, the compounds of the invention may exist in, and be isolated in, optically active or racemic form. The invention includes any optically active or racemic form of a compound of formula I which possesses pain-relieving properties. The synthesis of optically active forms may be carried out by standard techniques of organic chemistry well known in the art, for example by, resolution of a racemic form, by synthesis from optically active starting materials or by asymmetric synthesis. It will also be appreciated that certain compounds of formula I may exist as geometrical isomers. The invention includes any geometrical isomer of a compound of formula I which possesses pain-relieving properties.

It will also be understood that certain compounds of the present invention may exist in solvated, for example hydrated, as well as unsolvated forms. It is to be understood that the present invention encompasses all such solvated forms which possess the property of relieving pain.

It will further be understood that the present invention encompasses tautomers of the compounds of the formula (I).

Preferably A is optionally substituted:
phenyl, naphthyl, thiadiazolyl, thienyl, pyridyl or pyrimidyl.

Preferably B is optionally substituted:
pyridyl, phenyl, thiazolyl, thienyl, pyridazinyl, or oxazolyl.

Most preferably A is optionally substituted:
phenyl or thienyl.

More preferably B is optionally substituted:
pyridyl, phenyl, thienyl, pyridazinyl or thiazolyl.

In particular A is optionally substituted phenyl.
In particular B is optionally substituted:
pyrid-2,5-diyl, pyridazin-3,6-diyl, phen-1,4-diyl or thien-2,5-diyl.

Most particularly B is optionally substituted pyridazin-3,6-diyl or pyrid-2,5-diyl.

Most preferably B is pyridazinyl.

When D is hydrogen, preferably B is optionally substituted: pyridyl, thienyl, pyridazinyl or thiazolyl.

Preferred optional substituents for ring carbon atoms in A, are halo, nitro, trifluoromethyl, cyano, amino, $C_{1-6}$alkoxy, carbamoyl, $C_{1-4}$alkylcarbamoyl, di($C_{1-4}$alkyl)carbamoyl, $C_{1-4}$alkanoylamino, $C_{1-6}$alkylS(O)$_p$, $C_{1-4}$alkanesulphonamido, benzenesulphonamido, $C_{1-6}$alkanoyl, $C_{1-4}$alkoxyimino$C_{1-4}$alkyl and hydroxyimino$C_{1-4}$alkyl.

Preferably, when A is a 6-membered ring, A is unsubstituted or substituted in the 4-position relative to —OD.

Preferred optional substituents for ring carbon atoms of B are halo, trifluoromethyl, $C_{1-4}$alkyl, amino, $C_{1-4}$alkylamino, di-$C_{1-4}$alkylamino, nitro, hydroxy, $C_{1-6}$alkoxy and cyano.

Preferably n is 0.

Preferably A is optionally substituted by one substituent.

More preferably A is unsubstituted or substituted by bromo, methanesulphonyl, fluoro, bromo or chloro.

Most preferably A is unsubstituted or substituted by bromo or chloro.

Preferably B is unsubstituted or substituted by one substituent.

Most preferably B is unsubstituted.

Preferably $R^1$ is carboxy, carbamoyl or tetrazolyl or $R^1$ is of the formula —CONR$^a$R$^{a1}$ wherein R$^a$ is hydrogen or $C_{1-6}$alkyl and R$^{a1}$ is $C_{1-6}$alkyl optionally substituted by hydroxy, $C_{2-6}$alkenyl, 1-morpholinyl, 1-piperidinyl, 1-pyrrolidinyl, pyridyl$C_{1-3}$alkyl or $R^1$ is of the formula —CONHSO$_2$R$^b$ wherein R$^b$ is optionally substituted $C_{1-6}$alkyl, phenyl or 5- or 6-membered heteroaryl.

In particular, $R^1$ is carboxy, tetrazolyl or of the formula —CONR$^a$R$^{a1}$ wherein R$^a$ is hydrogen and R$^{a1}$ is $C_{1-6}$alkyl optionally substituted by hydroxy or pyridylmethyl, or $R^1$ is of the formula —CONHSO$_2$R$^b$ wherein R$^b$ is $C_{1-6}$alkyl (optionally substituted by hydroxy or fluoro) phenyl (optionally substituted by acetamido), isoxazolyl (optionally substituted by methyl), or 1,3,4-thiadiazolyl(optionally substituted by acetamido).

Most preferably $R^1$ is carboxy, tetrazole or of the formula —CONHR$^{a1}$ wherein R$^{a1}$ is pyridylmethyl or $C_{1-4}$alkyl optionally substituted by hydroxy, or of the formula —CONHSO$_2$R$^b$ wherein R$^b$ is $C_{1-4}$alkyl, 3,5-dimethylisoxazol-4-yl or 5-acetamido-1,3,4-thiadiazol-2-yl.

In another aspect $R^1$ is carboxy, carbamoyl or tetrazolyl or $R^1$ is of the formula —CONR$^a$R$^{a1}$ wherein $R^1$ is hydrogen or $C_{1-6}$alkyl and R$^{a1}$ is $C_{1-6}$alkyl optionally substituted by hydroxy, $C_{2-6}$alkenyl, 1-morpholinyl, 1-piperidinyl, 1-pyrrolidinyl, pyridyl$C_{1-3}$alkyl or $R^1$ is of the formula —CONHSO$_2$R$^b$ wherein R$^b$ is optionally substituted: $C_{1-6}$alkyl or phenyl.

Preferably $R^2$ is hydrogen, methyl, ethyl, 2,2,2-trifluoroethyl, cyanomethyl, allyl or 3-propynyl.

More preferably $R^2$ is hydrogen, methyl, ethyl or propyl.
Yet more preferably $R^2$ is hydrogen or ethyl.
Most preferably $R^2$ is ethyl.
Preferably $R^3$ is hydrogen.
Preferably $R^4$ is hydrogen or methyl.
Preferably $R^5$ is hydrogen, methyl or chloro.
Preferably $R^6$ is hydrogen, methyl or chloro.
Preferably $R^7$ is hydrogen or methyl.

Preferably the 5–7 membered carbocyclic ring containing one double bond is optionally substituted by methyl.

More preferably the 5–7 membered carbocyclic ring containing one double bond is unsubstituted.

Preferably D is a 5–6 membered carbocyclic ring containing one double bond (optionally substituted by methyl) methyl substituted by a 5–6 membered carbocyclic ring containing one double bond (optionally substituted by methyl) or of the formula —CH$_2$C(R$^5$)=C(R$^6$)R$^7$.

Most preferably D is of the formula:

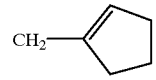 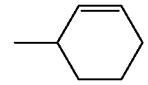

—CH$_2$CH=CH$_2$, —CH$_2$CH=CHMe, —CH$_2$CH=C(Me)$_2$, —CH$_1$C(Me)=CHMe, —CH$_2$C(Me)=CHMe, —CH$_2$C(Me)=CH$_2$ or —CH$_2$C(Cl)=CH$_2$.

In one aspect D is an optionally substituted 5–7 membered carbocyclic ring containing one double bond, $C_{1-3}$alkyl substituted by a 5–7 membered carbocyclic ring or of the formula —(CH$_2$)nCHR$^4$C(R$^5$)=C(R$^6$)R$^7$.

In another aspect D is hydrogen. A preferred class of compounds is that of the formula (II):

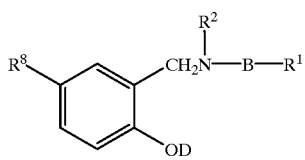 (II)

wherein
R$^1$, R$^2$ and D are as hereinabove defined, R$^8$ is hydrogen or as hereinabove defined for substituents for ring carbon atoms in A, and B is phenyl, thienyl, pyridazinyl, pyridyl, or thiazolyl.

It is to be understood that, insofar as certain of the compounds of formula (I) defined above may exist in optically active or racemic forms, by virtue of the compounds of the formula (I) containing an asymmetric carbon atom, the invention includes in its definition of active ingredient any such optically active or racemic form which possesses pain relieving properties. The synthesis of optically active forms may be carried out by standard techniques of organic chemistry well known in the art, for example by synthesis from optically active starting materials or by resolution of a racemic form. Similarly, pain relieving properties may be evaluated using the standard laboratory techniques referred to hereinafter.

An in vivo hydrolysable ester of a compound of the formula (I) containing carboxy or hydroxy group is, for example, a pharmaceutically acceptable ester which is hydrolysed in the human or animal body to produce the parent acid or alcohol for example, a pharmaceutically acceptable ester formed from the acid with a (1–6C)alcohol such as methanol, ethanol, ethylene glycol, propanol or butanol, or with a phenol or benzyl alcohol such as phenol or benzyl alcohol or a substituted phenol or benzyl alcohol wherein the substituent is, for example, a halo (such as fluoro or chloro), (1–4C)alkyl (such as methyl) or (1–4C) alkoxy (such as ethoxy) group. The term also includes α-acyloxyalkyl esters and related compounds which breakdown to give the parent hydroxy group. Examples of α-acyloxyalkyl esters include acetoxymethoxycarbonyl and 2,2-dimethylpropionyloxymethoxycarbonyl.

An in vivo hydrolysable ester of a compound of the formula (I) containing a hydroxy group is, for example, a pharmaceutically acceptable ester which is hydrolysed in the human or animal body to produce the parent alcohol. The term includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable value for an in vivo hydrolysable amide of a compound of the formula I containing a carboxy group is, for example, a N-(1–6C)alkyl or N,N-di-(1–6C)alkyl amide such as N-methyl, N-ethyl, N-propyl, N,N-dimethyl, N-ethyl-N-methyl or N,N-diethyl amide.

A suitable pharmaceutically-acceptable salt of a compound of the formula (I) is, for example, an acid-addition salt of a compound of the formula (I) which is sufficiently basic, for example an acid-addition salt with an inorganic or organic acid such as hydrochloric, hydrobromic, sulphuric, trifluoroacetic, citric or maleic acid; or, for example a salt of a compound of the formula (I) which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

In a further aspect the invention provides a process for preparing compounds of the formula (I) or pharmaceutically acceptable salts or in vivo hydrolysable amides or ester thereof, which comprises deprotecting a compound of the formula (III):

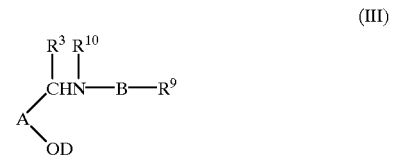 (III)

wherein R$^9$ is R$^1$ or protected R$^1$, R$^{10}$ is R$^2$ or protected R$^2$, R$^3$, n, A, B and D are as hereinabove defined, and any optional substituents are optionally protected and at least one protecting group is present;

and thereafter if necessary:
i) forming a pharmaceutically acceptable salt;
ii) forming an in vivo hydrolysable ester or amide;
iii) converting one optional substituent into another optional substituent.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

A suitable protecting group for a hydroxy group is, for example, an arylmethyl group (especially benzyl), a tri-(1–4C)alkylsilyl group (especially trimethylsilyl or tert-butyldimethylsilyl), an aryldi-(1–4C)alkylsilyl group (especially dimethylphenylsilyl), a diaryl-(1–4C)alkylsilyl group (especially tert-butyldiphenylsilyl), a (1–4C)alkyl group (especially methyl), a (2–4C)alkenyl group (especially allyl), a (1–4C)alkoxymethyl group (especially methoxymethyl) or a tetrahydropyranyl group (especially tetrahydropyran-2-yl). The deprotection conditions for the above protecting groups will necessarily vary with the choice of protecting group. Thus, for example, an arylmethyl group such as a benzyl group may be removed, for example, by hydrogenation over a catalyst such as palladium-on-charcoal. Alternatively a trialkylsilyl or an aryldialkylsilyl group such as a tert-butyldimethylsilyl or a dimethylphenylsilyl group may be removed, for example, by treatment with a suitable acid such as hydrochloric, sulphuric, phosphoric or trifluoroacetic acid, or with an alkali metal or ammonium fluoride such as sodium fluoride or, preferably, tetrabutylammonium fluoride. Alternatively an alkyl group may be removed, for example, by treatment with an alkali metal (1–4C)alkylsulphide such as sodium thioethoxide or, for example, by treatment with an alkali metal diarylphosphide such as lithium diphenylphosphide or, for example, by treatment with a boron or aluminium trihalide such as boron tribromide. Alternatively a (1–4C)alkoxymethyl group or tetrahydropyranyl group may be removed, for example, by treatment with a suitable acid such as hydrochloric or trifluoroacetic acid.

Alternatively a suitable protecting group for a hydroxy group is, for example, an acyl group, for example a (2–4C) alkanoyl group (especially acetyl) or an aroyl group (especially benzoyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide.

A suitable protecting group for an amino, imino or alkylamino group is, for example, an acyl group, for example a (2–4C)alkanoyl group (especially acetyl), a (1–4C) alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid, and an arylmethoxycarbonyl group such as a benzyloxycarbonyl group may be removed, for example, by hydrogenation over a catalyst such as palladium-on-charcoal.

A suitable protecting group for a carboxy group is, for example, an esterifying group, for example a (1–4C)alkyl group (especially methyl or ethyl) which may be removed, for example, by hydrolysis with a suitable base such as an alkali metal hydroxide, for example lithium or sodium hydroxide; or, for example, a tert-butyl group which may be removed, for example, by treatment with a suitable acid such as hydrochloric, sulphuric or phosphoric acid or trifluoroacetic acid.

In another aspect the compounds of the formula (I) or (III) may be prepared by:

a) when B is an activated heterocycle and $R^{10}$ is hydrogen or $C_{1-6}$alkyl, reacting a compound of the formula (IV) with a compound of the formula (V):

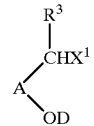
(IV)

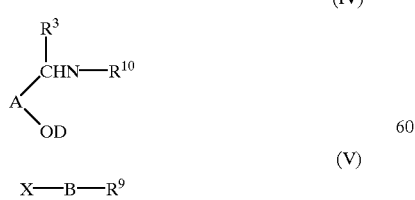
(V)

wherein A, B, $R^3$, $R^4$, $R^7$, $R^9$ and n are as hereinabove defined and X is a leaving group;

b) reacting a compound of the formula (VI) with a compound of the formula (VII):

(VI)

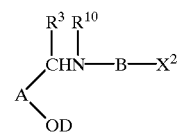
(VII)

c) converting $X^2$ to $R^9$ in a compound of the formula (VIII):

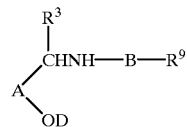
(VIII)

d) when $R^{10}$ is other than hydrogen, reacting a compound of the formula $R^{10}X^3$ with a compound of the formula (IX):

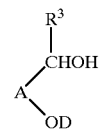

e) reacting a compound of the formula (X) with a compound of the formula (XI):

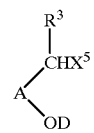
(X)

(XI)

f) reacting a compound of the formula (XII) with a compound of the formula (XIII):

(XII)

(XIII)

g) reacting a compound of the formula (XIV) with a compound of the formula (XV):

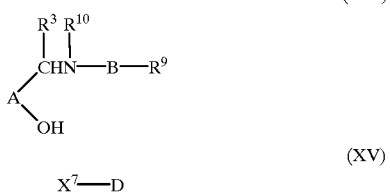

wherein $R^3$, $R^9$, $R^{10}$, A, B, D and n are as hereinabove defined,

X and $X^1$ are leaving groups, $X^2$ is a precursor of $R^9$, $X^3$ is a leaving group, $X^4$ is a removable activating group, $X^5$ is a leaving group, $X^6$ is an activating group and $X^7$ is halo or an activated hydroxy group; and thereafter if necessary:
i) removing any protecting groups;
ii) forming a pharmaceutically acceptable salt;
iii) forming an in vivo hydrolysable ester or amide;
iv) converting an optional substituent into another optional substituent.

Particular values for leaving groups include halogen, for example, chloro, bromo and iodo, sulphonates, for example tosylate, p-bromobenzenesulphonate, p-nitrobenzenesulphonate, methanesulphonate and triflate or phosphoric esters such as a diarylphosphoric ester.

Compounds of the formulae (IV) and (V) may be reacted together under standard conditions for example, in an aprotic solvent such as DMF in the presence of a weak base, in a temperature range of ambient to 180° C. Suitable values for X include, halo, tosylate, mesylate and triflate. In particular X is chloro or bromo.

The compounds of the formulae (VI) and (VII) may be reacted together under in an aprotic solvent such as DMF, in the presence of a base such as potassium carbonate or sodium hydride and in a temperature range of 0° C. to 100° C. Suitable values for $X^1$ include halo, tosylate, mesylate and triflate. In particular $X^1$ is bromo.

A precursor of $R^9$ is a group that can be converted into $R^9$.

Particular values for $X^2$ include cyano, carbamoyl, alkoxycarbonyl, carboxy and activated carboxy groups such as acid chlorides and activated esters.

The cyano group may be converted into a tetrazole ring by reacting, for example, with ammonium or tin azide in an aprotic solvent such as DMF, in a temperature range of 100° C. to 130° C. For further information on tetrazole synthesis see S. J. Wittenberger and B. J. Donner JOC, 1993, 58, 4139–4141; B E Huffet al, Tet. Lett, 1993, 50, 8011–8014; and J. V. Duncia et al, JOC 1991, 56, 2395–2400.

Alkoxycarbonyl may be converted into a carboxy group by acid or base hydrolysis. For example, base hydrolysis may be carried out in an organic solvent such as methanol or THF in a temperature range of ambient to 100° C., in the presence of sodium hydroxide or potassium hydroxide.

Acid hydrolysis may, for example, be carried out in neat formic acid or neat trifluoroacetic acid optionally in an inert organic solvent such as dichloromethane.

An alkoxycarbonyl or an activated carboxy group, such as an acid chloride or activated ester, or an acyl group such as an alkanoyl group may be converted to an amide group by reacting with the appropriate amine in an inert solvent such as DMF or dichloromethane, in a temperature range of 0° C. to 150° C., preferably around ambient temperature, in the presence of a base such as triethylamine.

The compounds of the formulae (IX) and $R^{10}X^3$ can be reacted together in an aprotic solvent such as DMF in the presence of a base such as sodium carbonate or sodium hydride. Suitable values for $X^3$ are halo, tosylate, mesylate and triflate, in particular halo such as iodo.

The reaction between compounds of the formulae (X) and (XI) is conveniently carried out under mild conditions known for the Mitsunobu reaction, for example in the presence of di ($C_{1-4}$alkyl)azocarboxylate and triphenylphosphine or $1^1,1^1$-(azodicarbonyl)dipiperidine and tributylphosphine (Tet. Lett. 34, 1993, 1639–1642) in an inert solvent such as toluene, benzene, tetrahydrofuran or diethylether, in particular toluene. Examples of removable activating groups are tert-butyloxycarbonyl and trifluoroacetyl.

Compounds of the formulae (XII) and (XIII) are generally reacted together in the presence of a strong base such as sodium hydride, lithium diisopropylamine or LiN(SiMe3)2, in DMF or an etherial solvent such as ethyl ether or THF in a temperature range of −78° C. to ambient temperature. Suitable values for $X^5$ are halogen, for example, methanesulphonate to tosylate. Examples of activating groups for $X^6$ include tert-butyloxycarbonyl, halogen and trifluoroacetyl.

Suitable leaving groups for $X^7$ include tosylate, mesylate, triflate and halo, for example chloro or bromo. The reaction between compounds of the formulae (XIV) and (XV) may be performed in an inert organic solvent such as acetone or DMF, in a temperature range of ambient temperature to 60° C., in the present of a mild base. For example, when $X^7$ is bromo, reacting (XIV) and (XV) together in DMF, at ambient temperature in the presence of a base such as potassium carbonate. Alternatively a phase transfer system could be used. $X^7$ can be hydroxy which is activated in situ using the Mitsunobu reaction (O. Synthesis, 1981, 1.).

Compounds of the formula (XIV) wherein $R^9$ is $R^1$ and $R^{10}$ is $R^2$ have pain-relieving properties in their own right.

The compounds of the formula (VIII) can be prepared using processes a), b), d), e), f) or g) from the appropriate starting material wherein $R^9$ is replaced with $X^2$.

The compounds of the formula (IX) may be prepared by using any one of processes a), b), c), e), p) or g) from the appropriate starting materials wherein $R^{10}$ is hydrogen.

The compounds of the formula (XI) can be readily prepared from compounds of the formula (VI).

The compounds of the formulae (V), (VI), (XI), (XIII) and (XV) are generally known in the art or can be made by methods analogous to or similar to those used in the examples or those known in the art for related compounds. Certain compounds of the formula (V), wherein X is chloro or bromo, can be prepared by converting an oxo group in the ring system into chloro or bromo by reacting the oxo ring system with a chlorinating agent, such as sulphonyl chloride, phosphorous trichloride, phosphorous pentachloride or P(O)Cl$_3$ or bromonating agent such as phosphorous tribromide or P(O)Br$_3$, in an inert aprotic solvent.

It is also possible to synthesise certain intermediates and even protected compounds using primarly ring synthesis. Here, reference is made to the compendium 'The Chemistry of Heterocyclic Compounds' E. C. Taylor and A. Weissberger (published by John Wiley and Sons) and 'Comprehensive Heterocyclic Chemistry', A. R Katritsky and C. W Rees (published by Pergamon Press).

Compounds of the formulae (IV), (VII), (VIII), (IX), (X) and (XII) can be prepared by reacting a compound of the formula (XV) with the appropriate hydroxy precursor of the compounds of the formula (IV), (VII), (VIII), (IX), (X), (XII) or (XIV) using similar reaction conditions to those described for process g).

Compounds of the formula (XV) can be prepared from appropriate starting materials by forming the —CH(R$^3$)N ($R^{10}$)—B—$R^9$ group using a similar process to one of processes a), b), c), d), e) or f).

Alternatively, the compound of the (XV) in which $R^{10}$ is hydrogen can be prepared by reducing a compound of the formula (XVI):

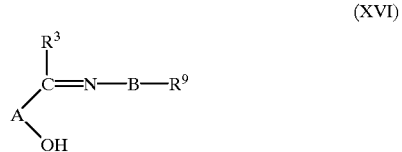

(XVI)

wherein $R^3$–$R^7$, $R^9$ and n are as hereinabove defined.

Compounds of the formula (XVI) can be reduced using agents as sodium borohydride or sodium cyanoborohydride. The compounds of the formula (XVI) can be prepared by reacting a compound of the formula (VI) with a compound of the formula (XVII):

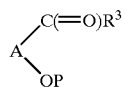

wherein $R^3$ is as hereinabove defined and P is a hydroxy protecting group and thereafter deprotecting the hydroxy group.

The reaction between compounds of the formula (VI) and (XVII) can be carried out under standard conditions known in the art for the formation of an imine (Schiffs base), which can be reduced in situ. For example, imine formation and reduction in situ can be carried out in an inert solvent such as toluene or tetrahydrofuran, in the presence of a reducing agent such as sodium cyanoborohydride ($NaCNBH_3$) under acidic conditions (Synthesis 135, 1975; Org. Prep. Proceed. Int. 11, 201, 1979).

Optional substituents may be converted into other optional substituents. For example an alkylthio group may be oxidised to an alkylsulphinyl or alkysulphonyl group, a nitro group reduced to an amino group, a hydroxy group alkylated to a methoxy group, or a bromo group converted to an alkylthio group.

Various substituents may be introduced into compounds of the formulae (I) and (III) and intermediates in the preparation of compounds of the formulae (I) and (III), when appropriate, using standard methods known in the art. For example, an acyl group or alkyl group may be introduced into an activated benzene ring using Friedel-Crafts reactions, a formyl group by formulation with titanium tetrachloride and dichloromethyl ethyl ether, a nitro group by nitration with concentrated nitric acid concentrated sulphuric acid and bromination with bromine or tetra(n-butyl) ammonium tribromide.

It will be appreciated that, in certain steps in the reaction sequence to compounds of the formula (I), it will be necessary to protect certain functional groups in intermediates in order to prevent side reactions. Deprotection may be carried out at a convenient stage in the reaction sequence once protection is no longer required.

As stated hereinbefore compounds of the formula (I) are antagonists of the pain enhancing effects of E-type prostaglandins and of value in the relief of mild to moderate pain which, for example, accompanies inflammatory conditions such as rheumatoid arthritis and osteoarthritis. Certain properties of the compounds may be demonstrated using the test procedures set out below:

(a) an in-vitro guinea pig ileum assay which assesses the inhibitory properties of a test compound against $PGE_2$-induced contractions of the ileum; ileum was immersed in oxygenated Krebs solution containing indomethacin (4 μg/ml) and atropine (1 μM) and which was maintained at 37° C.; the ileum was subject to a tension of 1 g; a control dose response curve for $PGE_2$-induced contraction of the ileum was obtained; test compound (dissolved in dimethylsulphoxide) was added to the Krebs solution and a dose response curve for the $PGE_2$-induced contraction of the ileum in the presence of the test compound was obtained; the $pA_2$ value for the test compound was calculated;

(b) an in-vivo assay in mice which assesses the inhibitory properties of a test compound against abdominal constriction response induced by the intraperitoneal administration of a noxious agent such as dilute acetic acid or phenylbenzoquinone (hereinafter PBQ) using the procedure disclosed in European Patent Application No. 0218077.

Although the pharmacological properties of the compounds of the formula I vary with structural change as expected, in general activity possessed by compounds of the formula I may be demonstrated at the following concentrations or doses in one or more of the above-mentioned Tests (a) and (b):

Test(a): $pA_2 > 5.3$;

Test (b): $ED_{30}$ in the range, for example, 0.01–100 mg/kg orally.

No overt toxicity or other untoward effects were noted in Test (b) when compounds of the formula I are administered at several multiples of their minimum inhibitory dose.

Prostaglandin receptors and in particular receptors for $PGE_2$ have been tentatively characterised by Kennedy et al. (Advances in Prostaglandin, Thromboxane and Leukotriene Research, 1983, 11, 327). The known $PGE_2$ antagonist SC-19220 blocks the effect of $PGE_2$ on some tissues such as guinea pig ileum or dog fundus but not on other tissues such as the cat trachea or chick ileum. Those tissues which did possess SC-19220 sensitive mediated effects were said to possess $EP_1$ receptors. Based on this compounds of the present invention, possessing activity in Test (a), are $EP_1$ antagonists.

According to a further feature of the invention there is provided a pharmaceutical composition which comprises a compound of the formula (I) or an in-vivo hydrolysable ester thereof or an amide thereof, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel, spray or aqueous or oily solution or suspension; for nasal use, for example a snuff, nasal spray or nasal drops; for vaginal or rectal use, for example a suppository or rectal spray; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a compound of the formula (I) or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition.

According to a further feature of the invention there is provided a compound of the formula (I) or an in-vivo hydrolysable ester or amide or a pharmaceutically-acceptable salt thereof, for use in a method of treatment of the animal (including human) body by therapy.

According to a further feature of the invention there is provided the use of a compound of the formula I, or an in-vivo hydrolysable ester or amide or a pharmaceutically-acceptable salt thereof, in the manufacture of a medicament for use in the relief of pain in the animal (including human) body.

According to a further feature of the invention there is provided a method for the relief of pain in the animal (including human) body in need of such treatment which comprises administering to said body an effective amount of a compound of the formula I, or an in-vivo hydrolysable ester or amide or a pharmaceutically-acceptable salt thereof.

As mentioned above, a compound of the formula (I) is useful in treating the pain which, for example, accompanies inflammatory conditions such as rheumatoid arthritis and osteoarthritis. In using a compound of the formula I for therapeutic or prophylactic purposes it will generally be administered so that a daily dose in the range, for example, 0.1 mg to 75 mg per kg body weight is received, given if required in divided doses. In general lower doses will be administered when a parenteral route is employed. Thus, for example, for intravenous administration, a dose in the range, for example, 0.05 mg to 30 mg per kg body weight will generally be used. Similarly, for administration by inhalation, a dose in the range, for example, 0.05 mg to 25 mg per kg body weight will be used.

Although the compounds of the formula (I) are primarily of value as therapeutic agents for use in warm-blooded animals (including man), they are also useful whenever it is required to antagonise the effects of $PGE_2$ at the $EP_1$ receptor, based on test a). Thus, they are useful as pharmacological standards for use in the development of new biological tests and in the search for new pharmacological agents.

By virtue of their ability to relieve pain, the compounds of the formula I are of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicylic acid, ibuprofen, sulindac, tolmetin and piroxicam. Co-administration of a compound of the formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the formula (I), or an in-vivo hydrolysable ester or amide or pharmaceutically-acceptable salt thereof, in conjunction or admixture with a cyclooxygenase inhibitory non-steroidal anti-inflammatory agent, and a pharmaceutically-acceptable diluent or carrier.

The compounds of the invention may also be used with other anti-inflammatory agents such as an inhibitor of the enzyme 5-lipoxygenase (such as those disclosed in European Patent Applications Nos. 0351194, 0375368, 0375404, 0375452, 0375457, 0381375, 0385662, 0385663, 0385679, 0385680).

The compounds of the formula (I) may also be used in the treatment of conditions such as rheumatoid arthritis in combination with antiarthritic agents such as gold, methotrexate, steroids and penicillamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compositions of the invention may in addition contain one or more other therapeutic or prophylactic agents known to be of value for the treatment of pain. Thus for example, a known opiate pain-killer (such as dextropropoxyphene, dehydrocodeine or codeine) or an antagonist of other pain or inflammation mediators, such as bradykinin, takykinin and calcitonin gene related peptides (CGRP), or an alpha$_2$-adrenoceptor agonist, a GABA$_B$ receptor agonist, a calcium channel blocker, a sodium channel blocker, a CCK$_B$ receptor antagonist, a neurokinin antagonist or an antagonist and modulator of the action of glutamamte at the NMDA receptor may usefully also be present in a pharmaceutical composition of the invention. These compositions may be useful in the treatment of mild, moderate or, in the case of certain combinations, even severe pain.

The compounds of the present invention may also be adminstered in bone diseases such as osteoporosis with calcitonin and bisphosphonates.

The invention will now be illustrated in the following non-limiting Examples in which, unless otherwise stated:

(i) evaporations were carried out by rotary evaporations in vacuo and work-up procedures were carried out after removal or residual solids by filtration;

(ii) yields are given for illustration only and are not necessarily the maximum attainable;

(iii) the end-products of the formula I have satisfactory microanalysis and their structures were generally confirmed by NMR and mass spectral techniques;

(iv) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture;

(v) the following abbreviations have been used:
DMF N,N-dimethylformamide;
THF tetrahydrofuran
DMSO dimethylsulphoxide
MPLC medium pressure liquid chromatography
TFAA trifluoroacetic anhydride

EXAMPLE 1

2-[N-(5-Bromo-2-(2-chloroallyloxy)benzyl)-N-ethylamino]-5-pyridylcarboxylic acid A solution of methyl 2-[N-(5-bromo-2-(2-chloroallyloxy)-benzyl-N-ethylamino]-5-pyridylcarboxylate (reference example 1) (0.8 g) (2.0 mmol) in methanol (3 ml) and THF (3 ml) was heated with sodium hydroxide (2N, 5 ml). The reaction was stirred at 40° C. for 18 hours. The solution was evaporated at reduced pressure and water was added. The suspension was acidified with acetic acid and left to stir for 30 minutes. The precipitate was filtered and washed with water and air dried to give the title compound as white solid (0.7 g).

MP: 207–209° C. MS: (FAB+): 425 (M+H)⁺; NMR: (200 MHz, DMSO-d₆) δ: 1.13 (t, 3H); 3.61 (q, 2H); 4.77 (s, 2H); 4.82 (s, 2H); 5.55 (d, 1H); 5.76 (d, 2H); 6.65 (d, 1H); 7.15 (m, 2H); 7.41 (dd, 1H); 8.62 (d, 1H); 12.4 (bs, 1H).

EXAMPLE 2

The compounds in the following table were prepared using a similar method to that of example 1.

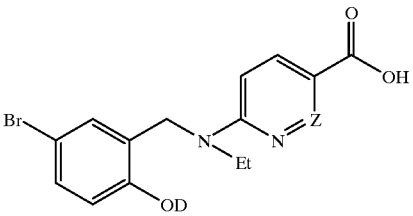

| Z | D | Footnote |
|---|---|---|
| CH | —CH(Me)CH=CH₂ | a |
| CH | —CH₂CH=CHMe | b |
| CH | —CH₂C(Me)=CH₂ | c |
| CH | —CH₂CH₂CH=C(Me)₂ | d |
| CH | —CH₂CH=C(Me)₂ | e |
| CH | —CH₂CH₂CH=CH₂ | f |
| CH |  | g |
| CH |  | h |
| CH |  | i |
| CH |  | j |
| CH | —CH₂C(Cl)=CHCl(Z) | k |
| CH | —CH₂C(Cl)=CHCl (E:Z, 85:15) | l |
| CH | —CH₂CH=CH₂ | m |
| CH | —CH₂C(Me)=CHMe | n |
| N | —CH₂C(Me)=CH₂ | o |

-continued

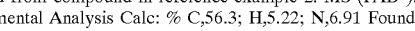

| Z | D | Footnote |
|---|---|---|
| N | —CH₂CH=CH₂ | p |
| N | —CH₂CH=CHCH₃ | q |

Footnotes:
a) Prepared from compound in reference example 2. MS (FAB⁺): 405 [M + H]⁺ Elemental Analysis Calc: % C,56.3; H,5.22; N,6.91 Found: % C,56.1; H5.3; N,6.7 NMR: (200 MHz, CDCl₃) δ: 1.21 (t, J = 7 Hz, 3H); 1.44 (d, J = 6 Hz, 3H); 3.62 (q, 2H); 4.75 (m, 3H); 5.22 (m, 2H); 5.95 (m, 1H); 6.42 (d, J = 9 Hz, 1H); 6.75 (dd, J = 3,8 Hz, 1H); 7.13 (m, 1H); 7.26 (m, 1H); 8.0 (m, 1H); 8.87 (d, J = 3 Hz, 1H).
b) Prepared from compound in reference example 2 Mpt: 167–169° C. MS (FAB⁺): 405 [M + H]⁺ Elemental Analysis: Calc: % C,56.3; H,5.22; N,6.91 Found: % C,56.1; H,5.3; N,6.7 NMR: (mixture or E + Z) δ: 1.12 (t, J = 7 Hz, 3H); 1.72 (dd, J = 6, 1 Hz, 3H); 3.6 (q, J = 7 Hz, 2H); 4.55 (d, J = 6 Hz, 1.6H); 4.68 (m, 2.4H); 5.75 (m, 2H); 6.63 (d, t = 8 Hz, 1H); 7.0 (m, 2H); 7.38 (dd, J = 3, 8 Hz, 1H); 7.86 (dd, J = 3, 8 Hz, 1H); 8.62 (d, J = 3 Hz, 1H), 12.38 (s, 1H).
c) Prepared from compound in reference example 2 Mpt: 189–195° C. MS (FAB⁺): 405 (M + H)⁺ Elemental Analysis: Calc: % C,56.3; H,5.22; N,6.91; Found % C,56.3; H,5.3; N,6.6; NMR (200 MHz, DMSO-d₆) δ: 1.14 (t, J = 7 Hz, 3H); 1.8 (s, 3H); 3.63 (q, J = 7 Hz, 2H); 4.45 (s, 2H); 4.98 (bs, 1H); 5.1 (bs, 1H); 6.64 (d, J = 9 Hz, 1H); 6.9 (d, J = 9 Hz, 1H); 7.03 (d, J = 3 Hz, 1H); 7.38 (dd, J = 3, 8 Hz, 1H); 7.92 (dd, J = 8, 3 Hz, 1H), 8.63 (d, J = 3 Hz, 1H); 12.35 (bs, 1H).
d) Prepared from compound in reference example 2 MS (FAB+): 433 (M + H)⁺ NMR (200 MHz, DMSO-d₆) δ: 1.11 (t, J = 7 Hz, 3H); 1.61 (s, 3H); 1.68 (s, 3H); 2.41 (q, J = 7 Hz, 2H); 3.59 (q, J = 7 Hz, 2H); 4.00 (t, J = 7 Hz, 2H), 4.7 (s, 2H); 5.21 (m, 1H); 6.64 (d, J = 9 Hz, 1H); 6.98 (d, J = 9 Hz, 1H), 7.05 (d, J = 2.5 Hz, 1H); 7.38 (dd, J = 2.5, 9 Hz, 1H); 7.91 (dd, J = 2,9 Hz, 1H); 8.61 (d, J = 2 Hz, 1H).
e) Prepared from compound in reference example 2 MS (FAB ⁺): 433 (M + Na)⁺ NMR (200 MHz, DMSO-d₆) δ: 1.09 (t, J = 7 Hz, 3H); 1.72 (s, 3H); 1.75 (s, 3H); 3.55 (m, 2H); 4.61 (m, 4H); 5.55 (m, 1H); 6.4 (d, J = 9 Hz, 1H); 7.00 (m, 2H); 7.35 (dd, J = 3,9 Hz, 1H); 7.87 (dd, J = 3,9 Hz, 1H); 8.5 (d, J = 3 Hz, 1H).
f) Prepared from compound in reference example 2 MS (FAB⁺) 405 (M + H)⁺ NMR (200 MHz, DMSO-d₆): δ: 1.11 (t, J = 7 Hz, 3H); 3.59 (q, J = 7 Hz, 2H); 4.09 (t, J = 6 Hz, 2H); 4.71 (s, 2H); 5.13 (m, 2H); 5.90 (m, 1H); 6.63 (d, J = 9 Hz, 1H); 7.03 (m, 2H); 7.37 (dd, J = 9 Hz, 2 Hz, 1H); 7.91 (dd, J = 2, 9H, 1H); 8.61 (d, J = 2 Hz, 1H): 12.37 (bs, 1H). (2H obscured by solvent)
g) Prepared from compound in reference example 2 Mpt: 167° C. MS: 431 (M + H)+ NMR (200 MHz, DMSO-d₆): δ 1.03 (t, J = 7 Hz, 3H); 1.65 (m, 4H); 1.83 (m, 2H); 3.51 (q, J = 7 Hz, 2H); 4.6 (s, 2H); 4.86 (m, 1H); 5.76 (m, 1H); 5.9 (m, 1H); 6.54 (d, J = 9 Hz, 1H); 7.00 (m, 2H); 7.29 (dd, J = 2.5, 9 Hz, 1H); 7.83 (dd, 2.3 Hz, 9 Hz, 1H); 8.52 (d, 2H).
h) Prepared from compound in reference example 4 Mpt: 94–100° C. MS: 445 (M + H)⁺ Elemental Analysis: Calc: % C,59.3; H,5.7; N,6.3; Found: % C,58.8; H,5.7; N,6.0 NMR (200 MHz, DMSO-d₆) δ: 1.1 (t, J = 7 Hz, 3H); 1.7 (m, 6H); 1.95 (m, 13H); 3.58 (q, J = 7 Hz, 2H); 4.66 (s, 2H); 4.9 (bs, 1H); 5.56 (bs, 1H); 6.62 (d, J = 9 Hz, 1H) 7.07 (m, 2H); 7.37 (dd, J = 2 Hz, 9 Hz, 1H); 7.9 (dd, J = 2, 9 Hz, 1H); 8.6 (d, J = 2 Hz, 1H).
i) Prepared from compound in reference example 4 MS: 485 (M + H)+ NMR (400 MHz, DMSO-d₆): δ 1.10 (t, J = 7 Hz, 3H); 1.40 (m, 1H); 1.74 (m, 6H); 1.9 (m, 1H); 2.07 (m, 1H); 2.20 (m, 1H); 2.35 (m, 1H); 3.62 (q, J = 7 Hz, 2H); 4.77 (m, 5H); 5.05 (m, 1H); 5.57 (m, 1H); 6.62 (d, J = 9 Hz, 1H); 7.15 (m, 2H); 7.44 (m, 1H); 7.94 (m, 1H); 8.65 (m, 1H); 12.35 (bs, 1H).
j) Prepared from compound in reference example 4 Mpt: 94–98° C. MS (CI+): 473 (M + H)⁺ Elemental Analysis: Calc. % C,60.9; H,6.17; N,5.92 Found % C,60.8; H,6.2; N,6.1 NMR (250 MHz, DMSO-d₆): δ 0.95 (s, 3H); 1.0 (s, 3H); 1.1 (t, J = 7 Hz, 3H); 1.45 (m, 3H); 1.69 (s, 3H); 1.8 (m, 3H); 3.57 (q, J = 7 Hz, 2H); 4.68 (s, 2H); 4.93 (bs, 1H); 5.5 (bs, 1H); 6.6 (d, J = 9 Hz, 1H); 7.04 (m, 2H); 7.38 (dd, J = 2, 9 Hz, 1H); 7.9 (dd, J = 2,9 Hz, 1H); 8.6 (d, J = 2 Hz, 1H).

-continued

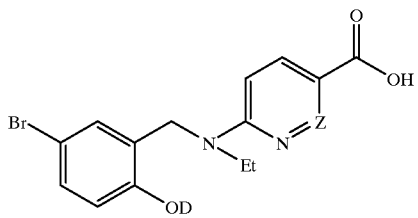

| Z | D | Footnote |
|---|---|----------| k) Prepared from compound in reference example 2 MS (CI+): 459 (M + H)+ Elemental Analysis: Calc % C,47.0; H,3.72; N,6.09; Found: % C,46.7; H,3.5; N,5.9. NMR (200 MHz, DMSO-d$_6$): δ 1.13 (t, 3H); 3.6 (q, 2H); 4.75 (s, 2H); 5.0 (s, 2H); 6.62 (d, 1H); 7.03 (s, ) 7.05 (d, J = 10 Hz) and 7.08 (d, J = 2.6 Hz) all together 3H); 7.42 (dd, J = 2.6, 10 Hz, 1H); 7.91 (dd, J = 2.6, 10 Hz, 1H); 8.60 (d, J = 2.5 Hz); 12.35 (bs, 1H).
l) Prepared from compound in reference example 2 MS (CI+): 459 [M + H]+ Elemental Analysis: Calc. % C,47.0; H,3.72; N,6.09; Found: % C,47.2; H,3.2; N,5.8. NMR (200 MHz, DMSO-d$_6$) δ: 1.13 (t, J = 6.6 Hz, 3H); 3.6 (q, J = 6.6 Hz, 2H); 4.75 (s, 2H); 4.9 (s, 1.7 H); 6.63 (d, J = 10 Hz); 7.07 (m, 2H); 7.25 (s, 0.85H); 7.4 (dd, J = 2.6, 10 Hz, 1H); 7.91 (dd, J = 2.6, 10 Hz, 1H); 8.60 (d, J = 2.6 Hz); 12.35 (bs, 1H).
m) Prepared from compound in reference example 6.
n) Prepared from compound in reference example 3.
o) Prepared from compound in reference example 4 Mp: 122.2–124.4° C. MS (ESP+): 406 (M + H)+ NMR (200 MHz, DMSO-d$_6$, HOAc-d$_4$) δ: 1.13 (t, J = 7 Hz, 3H); 1.73 (s, 3H); 3.63 (q, J = 7 Hz, 2H); 4.5 (s, 2H); 4.81 (s, 2H); 4.93 (s, 1H); 5.03 (s, 1H); 6.93 (d, J = 9 Hz, 1H); 7.03 (d, J = 9 Hz, 1H); 7.08 (d, J = 3 Hz, 1H); 7.33 (dd, J = 3, 9 Hz, 1H); 7.8 (d, J = 9 Hz, 1H).
p) Prepared from reference example 15 MS (ESP+): 392/394 (M + H)+ NMR (250 MHz, DMSO-d$_6$) δ: 1.15 (t, 3H); 3.17 (q, 2H); 4.64 (m, 2H); 4.83 (s, 2H); 5.25 (m, 1H); 5.42 (m, 1H); 6.05 (m, 1H); 7.0 (d, 1H); 7.1 (m, 2H); 7.40 (dd, 1H); 7.83 (d, 1H).
q) Prepared from reference example 28 NMR (200 MHz, DMSO-d$_6$) δ: 1.15 (t, 3H); 1.7 (d, 3H); 3.68 (q, 2H); 4.44 (d, 2H); 4.66 (d, 2H); 4.81 (s, 2H); 5.55–5.75 (m, 1H); 5.74–5.95 (m, 1H); 7.00 (d, 1H); 7.04–7.15 (m, 2H); 7.4 (dd, 1H); 7.82 (d, 1H).

EXAMPLE 3

6-[N-(5-Bromo-2-(2-chloroprop-2-en-1-yloxy) benzyl)-N-ethylamino]pyridazine-3-carboxylic acid n-Butyl 6-[N-(5-bromo-2-(2-chloroprop-2-en-1-yloxy) benzyl)-N-ethylamino]pyridazine-3-carboxylate (0.24 g, 0.5 mmol) was dissolved in methanol (2 ml), THF (2 ml) and treated with aqueous 1N sodium hydroxide solution (2 ml). The resultant solution was left at ambient temperature for 1.5 hours, evaporated to low bulk and the resultant precipitate dissolved in water and acidified with acetic acid to give a gummy precipitate. It was extracted with methylene chloride and the organic extracts dried and evaporated to give a gum. Trituration with ether yielded a solid which was filtered and sucked dry to give the title compound as a white solid (0.16 g, 75%).

MS: (+ve FAB): 426, 428 (M+H)+; NMR (200 MHz, DMSO-d$_6$) δ: 1.15 (t, J=6.3 Hz, 3H); 3.7 (q, J=6.3 Hz, 2H); 4.82 (s, 2H); 4.88 (s, 2H); 5.55 (d, J=1.25 Hz, 1H); 5.75 (d,J=1.25 Hz, 1H); 7.07 (d, J=9.6 Hz, 1H); 7.12 (d, J=8.3 Hz, 1H); 7.15 (d, J=2.1 Hz, 1H); 7.43 (dd, J=2.1, 8.3 Hz, 1H); 7.85 (d, J=9.6 Hz, 1H);

EXAMPLE 4

2-[N-(5-Bromo-2-hydroxybenzyl)-N-ethylamino] pyridine-5-carboxamide

2-[N-(5-Bromo-2-hydroxybenzyl)-N-ethylamino] pyridine-5-carboxylic acid (example 7) (1.8 g, 5.1 mmol) in tetrahydrofuran (40 ml) treated with carbonyl diimidazole (1.8 g, 11 mmol) and heated at gentle reflux for 4 hours. The mixture was cooled and added to 0.88 aqueous ammonia solution (60 ml), stirred for 1 hour at ambient temperature and then evaporated to low bulk. The resultant white solid was diluted with ice/water, filtered, washed with cold water and air dried to give the title compound as a white solid (1.93 g, 100%).

MS (CI+): 350, 352 (M+H)+.

EXAMPLE 5

5-[2-(N-(5-Bromo-2-(2-chloroprop-2-en-1-yloxy) benzyl)-N-ethylamino)-5-pyridyl]-tetrazole 2-[N-(5-Bromo-2-(2-chloroprop-2-en-1-yloxy)benzyl)-N-ethylamino]-5-cyanopyridine (reference example 8) (0.40 g, 0.96 mmol), in sieve-dried N-methyl pyrrolidone (10 ml) was treated with sodium azide (189 mg, 12.9 mmol) followed by triethylammonium chloride (208 mg, 1.49 mmol) and the mixture heated at 120° C. (oil bath) for 8 hours. The red solution was taken into ice/water (12 ml), acidified to pH 1–2 with concentrated hydrochloric acid, extracted with ethyl acetate (×2) and the combined extracts washed with water (×2), dried (MgSO$_4$) and evaporated to give a pale red gum (0.45 g). The gum was presorbed to silica (1.2 g) and purified by MPLC to give a colourless title compound as a gum which solidified (135 mg, 31%).

MS (ESP+): 449, 451 (M+H)+; NMR (200 MHz, DMSO-d$_6$) δ: 1.16 (t, J=6.7 Hz, 3H); 3.65 (q, J=6.7 Hz, 2H); 4.78 (s, 2H); 4.82 (s, 2H); 5.57 (d, J=1.7 Hz, 1H); 5.78 (d, J=1.7 Hz, 1H); 6.85 (d, J=9.3 Hz, 1H); 7.08 (d, J=9.3 Hz, 1H); 7.11 (d, J=2.7 Hz, 1H); 7.42 (dd, J=2.7, 9.3 Hz, 1H); 8.02 (dd, J=2, 9.3 Hz, 1H); 8.7 (d, J=2 Hz, 1H).

EXAMPLE 6

5-[2-(N-(5-Bromo-2-(2-methylprop-2-en-1-yloxy) benzyl)-N-ethylamino)-5-pyridyl]-tetrazole 2-[N-(5-Bromo-2-(2-methylprop-2-en-1-yloxy)benzyl)-N-ethylamino]-5-cyanopyridine (reference example 10) (0.45 g, 1.16 mmol) in N-methylpyrrolidone (12 ml) was treated with sodium azide (228 mg, 3.5 mmol) followed by triethylammonium chloride (251 mg, 1.8 mmol) and heated with stirring at 120° C. (oil bath) for 7 hours under an argon balloon. The resultant red solution was poured into ice/water (30 ml), acidified and extracted twice with ethyl acetate (total 50 ml). The combined organic extracts were washed twice with water, dried (MgSO$_4$) and evaporated to give a brown gum. The gum was purified by MPLC to give the title compound as an off-white foam (150 mg, 30%).

MS (ESP+): 429, 431 (M+H)+; NMR: (200 MHz, DMSO-d$_6$) δ: 1.27 (t, J=6.25 Hz, 3H); 1.9 (s, 3H); 3.73 (q, J=6.25 Hz, 2H), 4.64 (s, 2H); 4.87 (s, 2H); 5.08 (s, 1H); 5.2 (s, 1H); 6.91 (d, J=8.75, 1H); 7.10 (d, J=8.3 Hz, 1H); 7.17 (d, J=2 Hz, 1H); 7.48 (dd, J=2, 8.3 Hz, 1H); 8.16 (dd, J=2, 8.75 Hz, 1H); 8.8 (d, J=2 Hz, 1H).

EXAMPLE 7

2-[N-(5-Bromo-2-hydroxybenzyl)-N-ethylamino] pyridine-5-carboxylic acid

A solution of methyl 2-[N-(5-bromo-2-hydroxybenzyl)-N-ethylamino]pyridine-5-carboxylate (see reference example 7) (10.2 g, 0.55 mmol) in THF (3 ml) and methanol (5 ml) was treated with 1N aqueous sodium hydroxide solution (2.7 ml) and was heated to 40° C. for 24 hours. The solvents were evaporated at reduced pressure, the residue treated with 1N acetic acid (2.7 ml) and the precipitate filtered, washed with water and air dried to give the title compound (0.17 g, 92%).

MS (FAB+): 351 (M+H)$^+$; NMR (200 MHz, DMSO-d$_6$) δ: 1.12 (t, J=7 Hz, 3H); 3.6 (q, J=7 Hz, 2H); 4.64 (s, 2H); 6.6 (d, J=9 Hz, 1H); 6.83 (d, J=9 Hz, 1H); 7.06 (d, J=2 Hz, 1H); 7.23 (dd, J=2, 9 Hz, 1H); 7.92 (dd, J=2, 9 Hz, 1H); 8.59 (d, J=2 Hz, 1H).

EXAMPLE 8

6-[N-(5-Bromo-2-hydroxybenzyl)-N-ethylamino] pyridazine-3-carboxylic acid

A solution of butyl 6-[N-(5-bromo-2-hydroxybenzyl)-N-ethylamino]pyridazine-3-carboxylate (reference example 11) (0.36 g, 1.0 mmol) in THF (4 ml) and methanol (4 ml) was treated with aqueous sodium hydroxide 1N (4 ml) and allowed to stand at ambient temperature for 1.5 hours. The reaction was evaporated to a small volume, diluted with water and acidified with acetic acid. After standing for 18 hours, the precipitate was filtered, washed with water and ether, and air dried to give the title compound as a white solid (0.26 g, 71%).

MS: (ESP+) 352/354 (M+H)$^+$; NMR (200 MHz, DMSO-d$_6$) δ: 1.15 (t, J=6.67 Hz, 3H); 3.68 (q, J=6.67 Hz, 2H); 4.75 (s, 2H); 6.83 (d, J=8.34 Hz, 1H); 7.10 (d, J=8.34 Hz, 1H); 7.13(d, J=2.33 Hz, 1H); 7.25 (dd, J=10.00, 2.33 Hz, 1H); 7.83 (d, J=10.00 Hz, 1H);

EXAMPLE 9

5-[6-(N-(5-Bromo-2-(2-methylprop-2-en-1-yloxy) benzyl)-N-ethylamino)pyridazinyl]-tetrazole 6-[N-(5-Bromo-2-(2-methylprop-2-en-1-yloxy)benzyl)-N-ethylamino]-3-cyanopyridazine (reference example 13) (0.52 g, 1.34 mmol) in N-methylpyrrolidone (13 ml) was treated with sodium azide (403 mg, 6.1 mmol) followed by triethylammonium chloride (537 mg, 3.9 mmol) and the mixture stirred under argon for 7 hours at 120° C. The mixture was then poured into water and acidified to around pH$_2$. It was then extracted twice with ethyl acetate and the combined organic extracts washed twice with water, dried and evaporated to give a solid. The solid was purified by MPLC, and triturated with a 1:1 mixture of diethyl ether/ ethyl acetate to give the title compound as an off-white solid (275 mg, 48%).

MS (ESP+): 430, 432 (M+H)$^+$; NMR (DMSO-d$_6$) δ: 1.17 (t, J=8.3 Hz, 3H); 1.77 (s, 3H); 3.72 (q, J=8.3 Hz, 2H); 4.55 (s, 2H); 4.85 (s, 2H); 4.97 (s, 1H); 5.08 (s, 1H); 7.00 (d, J=10.4 Hz, 1H); 7.22 (d, J=2.1 Hz, 1H); 7.25 (d, J=10.4 Hz, 1H); 7.40 (dd, J=10.4, 2.1 Hz, 1H); 8.0 (d, J=10.4 Hz, 1H).

EXAMPLE 10

5-[6-(N-(5-Bromo-2-(cyclohex-2-enyloxy)benzyl)-N-ethylamino]pyridazin-3-yl]tetrazole The title compound was prepared from the compound in reference example 14 using a similar method to that of example 9, save that purification by MPLC gave a gum which solidified on evaporation from dichloromethane and which was triturated, filtered and washed with diethyl ether and ethyl acetate to give the title compound as a white solid (43%).

MS (ESP+): 456, 458 (M+H)$^+$; NMR (DMSO-d$_6$) δ: 1.15 (t, J=6.7 Hz, 3H); 1.50–2.08 (3xm, 6H); 3.7 (q, J=6.7 Hz, 2H); 4.80 (s, 2H); 4.93 (m, 1H); 5.70–6.02 (m, 2H); 7.10 (d, J=10 Hz, 1H); 7.27 (dd, J=3.3, 10.0 Hz, 2H); 7.40 (dd, J=8.3, 3.3 Hz, 1H); 8.00 (d, J=10.0 Hz, 1H).

EXAMPLE 11

N-Propanesulphonyl-6-[N-(5-bromo-2-(2-methylprop-2-en-1-yloxy)benzyl)-N-ethylamino] pyridazine-3-carboxamide 6-[N-(5-Bromo-2-(2-methylprop-2-enyloxy)benzyl)-N-ethylamino]pyridazin-3-carboxylic acid (185 mg, 0.46 mmol) was dissolved in dichloromethane (20 ml), (1-(3-dimethylaminopropyl)-3-ethyl-carbodiimide hydrochloride (EDAC), dimethylaminopyridine, (DMAP) (111 mg, 0.91 mmol) and propanesulfonamide (68 mg, 0.55 mmol) were added. The mixture was stirred at ambient temperature under argon overnight, after which TLC (25% water/CH$_3$CN) suggested the reaction was complete. The reaction mixture was loaded directly onto a MPLC column (silica) and the title compound obtained by elution with 5% EtOH/CH$_2$Cl$_2$ then 5% EtOH/0.5% AcOH/CH$_2$Cl$_2$, as a clear oil which solidified on triturating with hexane to give a colourless powder (110 mg, 47%).

M.p. 113.5° C.; MS: 511 (M+H)$^+$; Elemental Analysis: Calc: % C, 49.3; H, 5.32; N, 11.0; Found: % C,49.1; H, 5.3; N, 10.6; NMR (200 MHz, DMSO-d$_6$) δ: 1.0 (t, 3H), 1.2 (t, 3H); 1.8 (m, 5H); 3.4 (m, 2H); 3.7 (q, 2H); 4.55 (s, 2H); 4.90 (s, 2H); 4.95 (s, 1H); 5.1 (s, 1H); 7.0 (d, 1H); 7.1 (m, 5H); 7.4 (m, 1H); 7.9 (d, 1H).

EXAMPLE 12

The compounds in the following table were prepared using a similar method to that of example 11.

| Compound No. | D | R$^b$ | Footnote |
|---|---|---|---|
| 1 | CH$_2$C(Me)=CH$_2$ | Phenyl | a |
| 2 | CH$_2$C(Cl)=CH$_2$ | Phenyl | b |
| 3 | " | CH$_2$CH$_2$CH$_3$ | c |
| 4 | " | " | d |
| 5 | " | Phenyl | e |

-continued

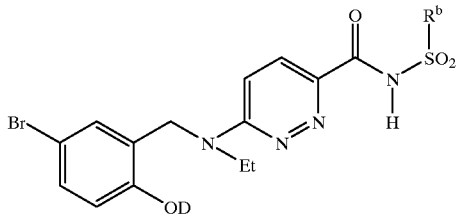

| Compound No. | D | $R^b$ | Footnote |
|---|---|---|---|
| 6 | $CH_2CH=CH_2$ | 3,5-dimethylisoxazol-4-yl | f |
| 7 | " | 5-acetylamino-1,3,4-thiadiazol-2-yl | g |

Footnotes
a) Prepared from the compound in example 2. Yield 61%. M.p. 162.5° C. MS: 545 (M + H)$^+$ Elemental Analysis: $C_{24}H_{25}BrN_4O_4S$. ½ $H_2O$ Calc. % C, 52.0; H, 4.69; N, 10.1 Found % C, 51.7; H, 4.4; N, 9.8 NMR (MHz, DMSO-$d_6$) δ: 1.15 (t, 3H); 1.8 (s, 3H); 3.6 (q, 2H); 4.5 (s, 2H); 4.8 (s, 2H); 4.9 (s, 1H); 5.1 (s, 1H); 7.0 (m, 3H); 7.2 (m, 1H); 7.5 (m, 3H); 7.7 (d, 1H); 7.9 (d, 2H).
b) Prepared from the compound in example 3. Yield 61%. M.p. 153.8° C. MS: 565 (M + H)$^+$ Elemental Analysis: Calc: % C, 48.8; H, 3.92; N, 9.9 Found: % C, 48.3; H, 3.7; N, 9.8 NMR (MHz, DMSO-$d_6$) δ: 1.15 (t, 3H); 3.65 (q, 2H); 4.75 (s, 2H); 4.8 (s, 2H); 5.5 (m, 1H); 5.75 (m, 1H); 7.1 (m, 3H); 7.5 (m, 4H); 7.75 (d, 1H); 7.9 (m, 1H).
c) Prepared from the compound in example 3. Yield 30%. M.p. 106.2° C. MS: 532 (M + H)$^+$ Elemental Analysis: Calc: % C, 45.2; H, 4.55; N, 10.5 Found: % C, 45.4; H, 4.2; N, 10.1 NMR (MHz, DMSO-$d_6$) δ 1.0 (t, 3H); 1.2 (t, 3H); 1.7 (m, 2H); 3.3 (m, 2H); 3.7 (q, 2H); 4.8 (s, 2H); 4.95 (m, 2H); 5.6 (m, 1H); 5.8 (m, 1H); 7.1 (m, 3H); 7.45 (m, 1H); 7.8 (d, 1H).
d) Prepared from the compound in example 16.1 Yield 19%. M.p. 105.2° C. Elemental Analysis: $C_{23}H_{29}BrN_4O_4S.1½ H_2O$ Calc: % C, 48.9; H, 5.6; N, 9.9 Found: % C, 49.2; H, 5.1; N, 9.5 NMR (MHz, DMSO-$d_6$) δ: 1.0 (m, 8H); 1.8 (m, 8H); 3.7 (q, 2H); 4.8 (s, 2H); 5.0 (m, 1H); 5.8 (m, 1H); 6.0 (m, 1H); 7.1 (m, 3H); 7.4 (m, 1H); 7.8 (d, 1H).
e) Prepared from the compound in example 16.1 Yield 28%. Mp. 148.9° C. Elemental Analysis: $C_{26}H_{27}BrN_4O_4S$. 31/2 $H_2O$ NMR (MHz, DMSO-$d_6$) δ: 1.1 (t, 3H); 1.8 (m, 6H); 3.6 (q, 2H); 4.7 (s, 2H); 4.8 (m, 2H); 5.7 (m, 1H); 5.9 (m, 1H); 7.1 (m, 3H); 7.4 (m, 1H); 7.55 (m, 3H); 7.7 (d, 1H); 7.9 (m, 2H).
f) Prepared from compound in example 2. Yield 80%. MS (ESP$^+$): 550/552 (M + H)$^+$ NMR (250 MHz., DMSO-$d_6$) δ: 1.14 (t, 3H); 2.4 (s, 3H); 2.6 (s, 3H); 3.6 (q, 2H); 4.62 (m, 2H); 4.86 (s, 2H); 5.25 (m, 1H); 5.39 (m, 1H); 6.0 (m, 1H); 7.0 (d, 1H); 7.13 (d, 1H); 7.2 (d, 1H); 7.4 (dd, 1H); 7.82 (d, 1H).
g) Prepared from compound in example 2. Yield 50%. MS (ESP$^+$): 596/598 (M + H)$^+$ NMR (250 MHz, DMSO-$d_6$) δ: 1.14 (t, 3H); 2.23 (s, 3H); 3.46 (q, 2H); 4.6 (m, 2H); 4.83 (s, 2H); 5.23 (m, 1H); 5.35 (m, 1H); 6.00 (m, 1H); 7.05 (d, 1H); 7.25 (d, 1H); 7.43 (dd, 1H); 7.57 (d, 1H); 8.05 (d, 1H); 12.85 (bs, 1H).

EXAMPLE 13

N-Benzenesulphonyl-2-[N-(5-bromo-2-(2-methylprop-2-en-1-yloxy)benzyl)-N-ethylamino]pyridine-5-carboxamide 2-[N-(5-Bromo-2-(2-methylprop-2-en-1-yloxy)benzyl)-N-ethylamino]pyridine-5-carboxylic acid (200 mg, 0.49 mmol) was dissolved in dichloromethane (20 ml) and dimethylamino pyridine (120 mg, 0.98 mmol), EDAC (1.41 mg, 0.74 mmol) and benzene sulfonamide (93 mg, 0.59 mmol) were added. The reaction mixture was stirred overnight under argon at ambient temperature whereupon it appeared complete by TLC (5% MeOH/$CH_2Cl_2$).

Dilute hydrochloric acid (1M, 40 ml), and water (40 ml) were added and the reaction mixture extracted with dichloromethane (3×90 ml). The combined organic layers were washed with water (40 ml), dried over magnesium sulphate and concentrated by evaporation. Purification by MPLC (silica, 2.5% EtOH/$CH_2Cl_2$ to 5% EtOH/$CH_2Cl_2$) gave a clear oil which solidified on trituration with ether or hexane to give the title compound as a white powder (26%).

M.p. 192.8° C.; MS: 544 (M+H)$^+$, 566 (M+Na)$^+$; Elemental Analysis: Calc: % C, 55.2%; H, 4.81; N, 7.72; Found: % C, 55.3%; H, 5.0; N, 7.4; NMR (MHz, DMSO-$d_6$) δ: 1.1 (t, 3H); 1.8 (s, 3H); 3.6 (q, 2H); 4.55 (s, 2H); 4.8 (s, 2H); 5.0 (s, 1H); 6.6 (d, 1H); 7.0 (m, 2H); 7.3 (dd, 1H); 7.6 (m, 3H); 7.9 (m, 3H); 8.55 (s, 1H).

EXAMPLE 14

The compounds in the following table were prepared using a similar method to that of example 13.

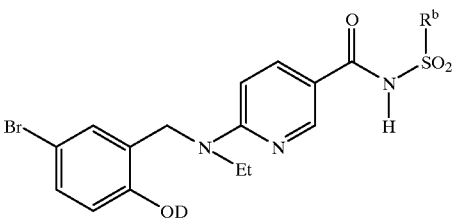

| Compound No. | D | $R^b$ | Footnote |
|---|---|---|---|
| 1 | $CH_2C(Me)=CH_2$ | $CH_2CH_2CH_3$ | a |
| 2 | $CH_2C(Cl)=CH_2$ | Phenyl | b |
| 3 | $CH_2C(Cl)=CH_2$ | $CH_2CH_2CH_3$ | c |

Footnotes
a) Prepared from example 2.14. Yield 36%. M.p. 125.5° C. MS: 510 (M + H)$^+$, 532 (M + Na)$^+$ NMR (MHz, DMSO-$d_6$) δ: 1.0 (t, 3H); 1.15 (t, 3H); 1.7 (m, 2H); 1.8 (s, 3H); 3.45 (m, 2H); 3.6 (m, 2H); 4.55 (s, 2H); 4.75 (s, 2H); 5.0 (s, 1H); 5.1 (s, 1H); 6.6 (d, 1H); 7.0 (m, 2H); 7.4 (m, 1H); 8.0 (m, 1H); 8.6 (d, 1H); 11.65 (bs, 1H).
b) Prepared from example 1. Yield 59%. M.p. 192.4° C. MS: 564 (M + H)$^+$, 586 (M + Na)$^+$ NMR (MHz, DMSO-$d_6$) δ 1.1 (t; 3H); 3.6 (q, 2H); 4.75 (s, 2H); 5.55 (m, 1H); 5.8 (m, 1H); 6.6 (d, 1H); 7.05 (m, 2H); 7.6 (m, 3H); 8.6 (m, 1H); 12.1 (brs, 1H).
c) Prepared from example 1. Yield 56%. M.p. 145.4° C. MS: 530 (M + H)$^+$, 553 (M + Na)$^+$ NMR (MHz, DMSO-$d_6$) δ: 1.0 (t, 3H); 1.2 (t, 3H); 1.8 (m, 2H); 3.5 (m, 2H); 3.7 (q, 2H); 4.75 (d, 4H); 5.55 (d, 1H); 5.8 (m, 1H); 6.65 (d, 1H); 7.0 (m, 2H); 7.4 (m, 1H); 8.0 (m, 1H); 8.6 (d, 1H).

EXAMPLE 15

6-[N-(5-Bromo-2-(2-methylprop-2-en-1-yloxy)benzyl)-N-ethylamino]pyridazine-3-carboxylic acid 6-[N-(5-Bromo-2-hydroxybenzyl)-N-ethylamino]pyridazine-3-carboxamide (843 mg, 2.4 mmol) was dissolved in DMF (15 ml) and added dropwise over ten minutes to a suspension of sodium hydride (192 mg, 2.88 mmol, 60% dispersion in mineral oil) in DMF (15 ml) and tetramethylethylenediamine (TMEDA, 0.72 ml, 8 mmol) under argon. The mixture was stirred for 1 hour, then 3-chloro-2-methylprop-1-ene (0.47 ml, 5.59 mmol) was added and the mixture heated to 100° C. and maintained at this temperature for 16 hours. The mixture was allowed to cool to ambient temperature, poured into water (150 ml) and adjusted to pH 5 with acetic acid. The aqueous mixture was extracted with ethyl acetate (3×120 ml) and the combined organic layers washed with 50% brine (100 ml), dried over $MgSO_4$ and evaporated to give a pale yellow oil.

This product was purified by MPLC (50% EtOAc/hexane, silica) to give 6-[N-(5-bromo-2-(2-methylprop-2-en-1-yloxy)benzyl]-N-ethylamino]pyridazine-3-carboxamide as a colourless foam (440 mg, 40%).

MS: 405 (M+H)$^+$; NMR (MHz, DMSO-$d_6$) δ: 1.3 (t, 3H); 1.8 (s, 3H); 3.8 (q, 2H); 4.4 (s, 2H); 4.8 (s, 2H); 5.0 (m, 1H);

5.1 (m, 1H); 5.6 (brs, 1H); 6.9 (m, 2H); 7.1 (d, 1H); 7.3 (m, 1H); 7.7 (brs, 1H); 7.9 (d, 1H).

6-[N-(5-Bromo-2-(2-methylprop-2-en-1-yloxy)benzyl)-N-ethylamino]pyridazine-3-carboxamide (430 mg, 1.09 mmol) was dissolved in THF/methanol (30 ml, 1:1) and sodium hydroxide solution added (2.9 ml, 2M, 5.8 mmol). The mixture was heated at reflux for 72 hours, allowed to cool and evaporated. The residue was dissolved in water (25 ml) and acetic acid added to pH-4. The solution was stirred for 16 hours and then the resulting colourless precipitate collected by filtration, washed with water and dried under vacuum to give the title compound as a colourless powder (387 mg, 87%).

MS: 406 (M+H)$^+$; NMR (MHz, DMSO-d$_6$) δ: 1.0 (t, 3H); 1.7 (s, 3H); 3.6 (q, 2H); 4.4 (s, 2H); 4.7 (s, 2H); 4.85 (s, 1H); 5.0 (s, 1H); 6.9 (d, 1H); 7.0 (m, 2H); 7.3 (m, 1H); 7.7 (d, 1H).

EXAMPLE 16

The compounds in the following table were prepared using a similar method to that of example 15.

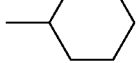

| Compound No. | D | MS | Footnote |
|---|---|---|---|
| 1 | CH$_2$C(Cl)=CH$_2$ | 426 (M + H)$^+$ | a) |
| 2 | cyclohexylmethyl | 432 (M + H)$^+$ | b) | a) NMR (DMSO-d$_6$) δ: 1.15 (t, 3H); 3.6 (q, 2H); 4.75 (s, 2H); 4.85 (s, 2H); 5.5 (m, 1H); 5.75 (m, 1H); 7.1 (m, 3H); 7.4 (m, 2H); 7.8 (d, 1H).
b) NMR (DMSO-d$_6$) δ: 1.1 (t, 3H); 1.7 (m, 3H); 2.0 (m, 3H); 3.7 (q, 2H); 4.7 (s, 2H); 4.9 (m, 1H); 5.8 (m, 1H); 6.0 (m, 1H); 7.0 (m, 3H); 7.3 (m, 1H); 7.8 (d, 1H).

EXAMPLE 17

N-(3,5-Dimethylisoxazol-4-ylsulphonyl)-6-[N-(5-bromo-2-(2-methylprop-2-en-1-yloxy)benzyl)-N-ethylamino]pyridazine-3-carboxamide 6-[N-(5-Bromo-2-(2-methylprop-2-en-1-yloxy)benzyl)-N-ethylamino]pyridazine-3-carboxylic acid (example 2, compound 15) (187 mg, 0.46 mmol) was dissolved in dichloromethane (20 ml) and (1-(3-dimethylaminopropyl)-3-ethyl-carbodiimide hydrochloride (EDAC),(133 mg, 0.69 mmol), dimethylaminopyridine (DMAP) (113 mg, 0.92 mmol) and 3,5-dimethylisoxazol-4-ylsulfonamide (98 mg, 0.56 mmol) were added. The mixture was stirred at ambient temperature under argon for 72 hours, after which TLC (25% water/methanol) suggested the reaction was complete. The reaction mixture was loaded directly onto a MPLC column (silica) and the title compound obtained by elution 2.5% ethanol/dichloromethane followed by 0.5% acetic acid/2.5% ethanol/dichloromethane as a gum which was triturated with hexane to give the title product as a solid (98 mg, 38%).

M.p. 119.8° C.; MS (ESP+): 564 (M+H)$^+$; Elemental Analysis: C$_{22}$H$_{26}$BrN$_5$O$_5$S; Calc: % C, 48.9; H, 4.64; N, 12.4; Found: % C,48.3; H, 4.6; N, 12.0; NMR (250 MHz, DMSO-d$_6$) δ: 1.15 (t, J=7 Hz, 3H); 1.8 (m, 2H); 2.35 (s, 3H); 2.65 (s, 3H); 3.7 (q, J=7 Hz, 2H); 4.5 (s, 2H); 4.8 (s, 2H); 4.95 (s, 1H); 5.15 (s, 1H); 7.0 (d, J=8.5 Hz, 1H); 7.15 (m, 2H); 7.4 (dd, J=2, 8 Hz, 1H); 7.8 (d, J=8.5 Hz, 1H).

EXAMPLE 18

6-[N-(5-Chloro-2-(2-methylprop-2-en-1-yloxy)benzyl)-N-ethylamino]pyridazine-3-carboxamide A mixture of N-ethyl-5-chloro-2-(2-methylprop-2-en-1-yloxy)benzylamine (reference example 16) (13.8 g, 50 mM), 6-chloropyridazine-3-carboxamide (7.9 g, 50 mM) and di-isopropylethylamine (20.0 ml, 115 mM) in DMF (50 ml) was stirred at reflux for 16 hours. The mixture was cooled and diluted with water (200 ml) giving an oil which was allowed to settle out (1 hour). The supernatant liquor was decanted and the residual brown gum dissolved in dichloromethane (250 ml) and washed with 2N hydrochloric acid (100 ml). The product was obtained by eluting the organic layer through silica, adjusting the solvent to dichloromethane/isopropanol (19:1) and collecting relevant fractions, which were combined and evaporated to give the title compound as a gum (10.5 g, 58%).

MS (ESP+): 361/362 (M+H)$^+$; NMR (200 MHz, DMSO-d$_6$) δ: 1.17 (t, J=7 Hz, 3H); 1.80 (s, 3H); 3.90 (q, J=7 Hz, 2H), 4.55 (s, 2H); 4.85 (s, 2H); 4.98 (s, 1H); 5.10 (s, 1H); 7.00 (d, J=2 Hz, 1H); 7.05 (d, J=9 Hz, 1H); 7.14 (d, J=9 Hz, 1H); 7.28 (dd, J=2, 9 Hz, 1H); 7.47 (broad s, 1H); 7.87 (d, J=9 Hz, 1H); 8.10 (broad s, 1H).

EXAMPLE 19

6-[N-(5-Chloro-2-(2-methylprop-2-en-1-yloxy)benzyl)-N-ethylamino]pyridazine-3-carboxylic acid A mixture of 6-[N-(5-Chloro-2-(2-methylprop-2-en-1-yloxy)benzyl)-N-ethylamino]-pyridazine-3-carboxamide (example 18) (10.5 g, 29.3 mol) and caustic liquor, 40% w/v (10 ml, 100 mmol) in ethanol (150 ml) was stirred at reflux for 16 hours. The solvent was evaporated at reduced pressure and the residue partitioned between 2N hydrochloric acid (70 ml) and dichloromethane (200 ml). The organic layer was dried over anhydrous magnesium sulphate, filtered and evaporated to give a brown gum (10.0 g), which was redissolved in ether (200 ml) and allowed to crystallise slowly over 12 hours to give the title compound as a pale yellow solid (4.6 g, 45%) m.p. 130–131° C.

MS (ESP+): 362/264 (M+H)$^+$; NMR (200 MHz, DMSO-d$_6$) δ: 1.17 (t, 7 Hz, 3H), 1.78 (s, 3H), 3.70 (q, J=7 Hz, 2H), 4.45 (s, 2H), 4.85 (s, 2H), 4.98 (s, 1H), 5.08 (s, 1H), 7.02 (d, J=2 Hz, 1H); 7.05 (d, J=8 Hz, 1H), 7.12 (d, J=9 Hz, 1H), 7.27 (dd, J=2, 8 Hz, 1H); 7.83 (d, J=9 Hz, 1H).

EXAMPLE 20

N-(2-(Pyrrolidino)ethanesulphonyl)-6-[N-(5-chloro-2-(2-methylprop-2-en-1-yloxy)benzyl)N-ethylamino]pyridazine-3-carboxamide A mixture of 6-[N-(5-chloro-2-(2-methylprop-2-en-1-yloxy)benzyl)-N-ethylamino]-pyridazine-3-carboxylic acid (example 19) (2.0 g, 5.5 mmol), 2-(pyrrolidino)ethanepyridine (20 mmol) and ethyl dimethylaminopropylcarbodi-imide hydrochloride (7.8 mmol) in dichloromethane (25 ml) containing DMF (5 ml)

was stirred at 40° C. for 16 hours. The mixture was diluted with dichloromethane (50 ml) and water (50 ml), stirred for 10 minutes and the organic layer was separated, washed with water (50 ml) and dried over anhydrous magnesium sulphate. Chromatography on silica, eluting with 5% methanol in dichloromethane gave the title compound (1.2 g, 42%).

MS (ESP+): 522/524 (M+H)$^+$; NMR (200 MHz, DMSO-$d_6$) δ: 1.16 (t, J=7 Hz, 3H); 1.78 (s, 3H); 2.00 (broad s, 4H), 3.20 m, 2H); 3.30 (broad s, 4H); 3.50 (m, 2H); 3.67 (q, J=7 Hz, 2H); 4.53 (s, 2H); 4.81 (s, 2H); 4.98 (s, 1H); 5.08 (s, 1H); 6.95–7.25 (m, 4H); 7.82 (d, J=8 Hz, 1H).

EXAMPLE 21

N-(2-(Morpholino)ethanesulphonyl)-6-[N-(5-chloro-2-(2-methylprop-2-en-1-yloxy)benzyl)-N-ethylamino]pyridazine-3-carboxamide The title compound was prepared by reacting 6-[N-(5-chloro-2-(2-methylprop-2-enyloxy)benzyl)-N-ethylamino]pyridazine-3-carboxylic acid (example 19) and 2-(morpholino)ethanesulphonamide using a similar method to that described in example 20 (yield 43%).

MS (ESP+): 538/540 (M+H)$^+$; NMR (200 MHz, DMSO-d6) δ: 1.17 (t, J=7 Hz, 3H); 1.78 (s, 3H); 2.55 (m, 4H); 2.87 (t, J=6 Hz, 2H); 3.40 (t, J=6 Hz, 2H); 3.55 (m, 4H); 3.68 (q, J=7 Hz, 2H); 4.53 (s, 2H); 4.83 (s, 2H); 4.97 (s, 1H); 5.08 (s, 1H); 6.97 (d, J=2 Hz, 1H); 7.03 (d, J=8 Hz, 1H); 7.12 (d, J=8 Hz, 1H); 7.25 (dd, J=2, 8 Hz, 1H); 7.86 (d, J=8 Hz, 1H).

EXAMPLE 22

6-[N-(5-Fluoro-2-(2-methylprop-2-en-1-yloxy)benzyl)-N-ethylamino]pyridazine-3-carboxylic acid The title compound was prepared from reference example 17 using a similar method to that of example 1 (Yield 74%). m.p. 121–2° C.

MS (ESP-): (M-H)-344; NMR (200 MHz, DMSO-$d_6$) δ: 1.18 (t, J=7 Hz, 3H), 1.80 (s, 3H); 3.70 (q, J=7 Hz, 2H); 4.52 (s, 2H); 4.85 (s, 2H); 4.97 (s, 1H); 5.10 (s, 1H); 6.80 (dd, J=2, 8 Hz, 1H); 7.0–7.13 (m, 3H); 7.83 (d, J=8 Hz, 1H); Analysis: Calc. % C, 62.6; H, 5.8; N, 12.2; Found C, 62.7; H, 5.9; N, 11.9.

EXAMPLE 23

6-[N-(5-Chloro-2-(cyclohexen-3-yloxy)benzyl)-N-ethylamino]pyridazine-3-carboxylic acid The title compound was prepared from reference example 18 using a similar method to that of example 1. The product was extracted with dichloromethane, dried over anhydrous magnesium sulphate and triturated with ether and hexane (Yield 38%).

MS (ESP+): 388/390 (M+H)$^+$; NMR (200 MHz, DMSO-$d_6$) δ: 1.13 (t, 3H); 1.70 (m, 3H); 1.85 (m, 1H); 2.00 (br s, 2H); 3.65 (q, 2H); 4.75 (s, 2H); 4.90 (br s, 1H); 5.80 (dd, 1H); 5.94 (dt, 1H); 7.04 (d, 1H); 7.07 (d, 1H); 7.13 (d, 1H); 7.25 (dd, 1H); 7.80 (d, 1H).

EXAMPLE 24

N-(3,5-Dimethylisoxazol-4-ylsulphonyl)-6-[N-(5-chloro-2-(cyclohexen-3-yloxy)benzyl)-N-ethylamino]pyridazine-3-carboxamide The title compound was prepared from 6-[N-(5-chloro-2-(cyclohexen-3-yloxy)benzyl)-N-ethylamino]pyridazine-3-carboxylic acid (example 23) and 3,5-dimethylisoxazol-4-ylsulphonamide using a similar method to that of example 11 (Yield 22%).

MS (ESP+): 546/548 (M+H)$^+$; NMR (200 MHz, DMSO-$d_6$) δ: 1.12 (t, 3H); 1.20 (m, 3H); 1.95 (m, 3H); 2.35 (s, 3H); 2.63 (s, 3H); 3.65 (q, 2H); 4.77 (s, 2H); 4.88 (br s, 1H); 5.77 (dd, 1H); 5.93 (dt, 1H); 7.02 (d, 1H); 7.10 (d, 1H); 7.12 (d, 1H); 7.25 (dd, 1H); 7.76 (d, 1H).

EXAMPLE 25

5-[6-(N-[5-chloro-2-(2-methylprop-2-en-1-yloxy)benzyl]-N-ethylamino)pyridazin-3-yl]tetrazole To 6-[N-(5-chloro-2-(2-methylprop-2-en-1-yloxy)benzyl)-N-ethylamino]-3-cyanopyridazine (reference example 19) in 1-methyl 2-pyrrolidinone (10 ml) was added sodium azide (330 mg, 5.1 mmol) and triethylamine hydrochloride (320 mg, 0.2 mmol) and the solution stirred at 150° C. for 3 hours. Water (50 ml) was added and the solution acidified with glacial acetic acid to pH 2. The resulting precipitate was isolated, dissolved in dichloromethane, dried over anhydrous magnesium sulphate, filtered and the solvent removed in vacuo to give a brown oil (140 mg). Trituration with ether alloed crystals of the title compound to form (50 mg, 17%).

MS: (ESP+): 386/388 (MH+); NMR (200 MHz, DMSO-$d_6$) δ: 1.16 (t, 3H); 1.28 (s, 3H); 3.71 (q, 2H); 4.54 (s, 2H); 4.85 (s, 2H); 4.97 (2, 1H); 5.08 (s, 1H); 7.05 (m, 2H); 7.27 (m, 2H); 8.02 (d, 1H).

EXAMPLE 26

N-(3,5-Dimethylisoxazol-4-ylsulphonl)-6-[N-(5-chloro-2-(2-methylprop-2-en-1-yloxy)benzyl)-N-ethylamino]pyridazin-3-carboxamide The title compound was prepared from 6-[N-(5-chloro-2-(2-methylprop-2-en-1-yloxy)benzyl)-N-ethylamino]pyridazin-3-carboxylic acid (example 19) (210 mg, 0.58 mmol) and 3,5-dimethylisoxazol-4-ylsulphonamide using a similar method to that of example 11. The title compound was purified by column chromatography (eluant: 5% propan-2-ol in dichloromethane) (80 mg, 27%).

MS: (ESP+): 520/522 (MH+); NMR (200 MHz, DMSO-$d_6$) δ: 1.13 (t, 3H); 1.78 (s, 3H); 2.28 (s, 3H); 2.55 (s, 3H); 3.62 (q, 2H); 4.02 (s, 2H); 4.78 (2, 2H); 4.98 (s, 1H); 5.08 (s, 1H); 6.92 (m, 2H); 7.03 (d, 1H); 7.24 (dd, 1H); 7.81 (d, 1H).

EXAMPLE 27

N-(Trifluoromethanesulphonyl)-6-[N-(5-chloro-2-(2-methylprop-2-en-1-yloxy)benzyl)-N-ethylamino]pyridazin-3-carboxamide The title compound was prepared from 6-[N-(5-chloro-2-(2-methylprop-2-en-1-yloxy)-benzyl)-N-ethylamino]pyridazin-3-carboxylic acid (example 19) and trifluoromethanesulphonamide using a similar method to that of example 11 (18%).

MS: (ESP+): 493/495 (MH+); NMR (200 MHz, DMSO-$d_6$) δ: 1.18 (t, 3H); 1.80 (s, 3H); 3.65 (q, 2H); 4.55 (s, 2H); 4.83 (s, 2H); 4.97 (s, 1H); 5.10 (s, 1H); 6.95 (d, 1H); 7.02 (m, 2H); 7.25 (dd, 1H); 7.80 (d, 1H).

EXAMPLE 28

N-(2-Carboxyphenyl)-6-[N-(5-chloro-2-(2-methylprop-2-en-1-yloxy)benzyl)-N-ethylamino]pyridazin-3-carboxamide The title compound was prepared from N-(2-methoxycarbonylphenyl)-6-[N-(5-chloro-2-(2-methylprop- 2-en-1-yloxy)benzyl)-N-ethylamino]pyridazin-3-carboxamide using a similar method to the one in Example 1(19%).

MS: (ESP+): 481/483 (MH+); NMR (200 MHz, DMSO-d$_6$) δ: 1.18 (t, 3H); 1.79 (s, 3H); 3.72 (q, 2H); 4.53 (s, 2H); 4.58 (s, 2H); 4.97 (s, 1H); 5.08 (s, 1H); 6.98 (d, 1H0; 7.03 (d, 1H); 7.20 (m, 3H), 7.62 (td, 1H); 7.97 (d, 1H); 8.04 (dd, 1H); 8.81 (d, 1H); 12.86 (s, 1H).

EXAMPLE 29

N-(1-Carboxyethyl)-6-[N-(5-chloro-2-(2-methylprop-2-en-1-yloxy)benzyl)-N-ethylamino] pyridazin-3-carboxamide The title compound was prepared as a gum from N-(1-methoxycarbonylethyl)-6-[N-(5-chloro-2-(2-methylprop-2-en-1-yloxy)benzyl)-N-ethylamino]pyridazin-3-carboxamide using a similar method to that of example 1. (15%)

MS: (ESP+): 433/435 (MH+); NMR (200 MHz, DMSO-d$_6$) δ: 1.15 (t, 3H); 1.42 (d, 3H); 1.78 (s, 3H); 3.69 (q, 2H); 4.45 (dt, 1H); 4.55 (s, 2H); 4.85 (s, 2H); 4.98 (s, 1H); 5.10 (s, 1H); 6.97 (d, 1H); 7.04 (d, 1H); 7.17 (d, 1H); 7.83 (d, 1H); 8.73 (d, 1H).

EXAMPLE 30

N-(α-Carboxybenzyl)-6-[N-(5-chloro-2-(2-methylprop-2-en-1-yloxy)benzyl)-N-ethylamino] pyridazin-3-carboxamide The title compound was prepared from N-(α-methoxycarbonylbenzyl)-6-[N-(5-chloro-2-(2-methylprop-2-en-1-yloxy)benzyl)-N-ethylamino]pyridazin-3-carboxamide using a similar method to that of example 1 (13%).

MS: (ESP+): 495/497 (MH+); NMR (200 MHz, DMSO-d$_6$) δ: 1.17 (t, 3H); 1.24 (s, 3H); 3.70 (q, 2H); 4.53 (s, 2H); 4.83 (s, 2H); 4.97 (s, 1H); 5.08 (s, 1H); 5.55 (d, 1H); 7.45 (m, 9H); 7.81 (d, 1H); 8.89 (d, 1H).

EXAMPLE 31

N-(3,5-Dimethylisoxazol-4-ylsulphonyl)-6-[N-(5-Chloro-2-allyloxybenzyl)-N-ethylamino]pyridazine-3-carboxamide The title compound was prepared from the corresponding carboxylic acid using a similar method to those in example 12, except that purification was achieved with column chromotography in propan-2-ol, methanoic acid and dichloromethane, followed by trituration with diethyl ether. (250 mg, 33%)

MS (ESP+): 506/508; NMR (250 MHz, DMSO-d$_6$) d: 1.13 (t, 3H); 2.27 (q, 3H); 2.58 (s, 3H); 3.64 (q, 2H); 4.63 (m, 2H); 4.78 (s, 2H); 5.28 (dd, J=10 Hz, 2 Hz, 1H); 5.43 (dd, J=16 Hz, 2 Hz, 1H); 6.04 (m, 1H); 6.95 (d, J=2 Hz, 1H) 6.97 (d, J=8 Hz, 1H); 7.03 (d, J=8 Hz, 1H) 7.24 (dd, J=2 Hz, 8 Hz, 1H); 7.79 (d, J=8 Hz, 1H).

EXAMPLE 32

6-[N-(5-Chloro-2-allyloxybenzyl)-N-ethylamino] pyridazine-3-carboxamide

The title compound was prepared using a similar method to that of example 18. (4.0 g, 35%).

MS (ESP+): 347/349 (MH+); NMR (250 MHz, DMSO-d$_6$) d: 1.16 (t, 3H); 3.67 (q, 2H); 4.64 (m, 2H); 4.81 (s, 2H); 5.27 (dd, J=10 Hz, 2Hz, 1H); 5.42 (dd, J=16 Hz, 2 Hz, 1H); 6.04 (m, 1H); 6.99 (d, J=2 Hz, 1H); 7.05 (d, J=8 Hz , 1H); 7.13 (d, J=9 Hz, 1H); 7.25 (dd, J=2 Hz, 8 Hz, 1H); 7.41 (br. s, 1H); 7.82 (d, J=9 Hz, 1H); 8.06 (br. s, 1H).

EXAMPLE 33

6-[N-(5-Chloro-2-allyloxybenzyl)-N-ethylamino] pyridazine-3-carboxylic acid

The title compound was prepared from the corresponding amide (example 32) using a similar method to that outlined in example 19, except that crystallisation was achieved with dichloromethane/diethyl ether/hexane followed by trituration with diethyl ether (900 mg, 45%).

MS (ESP+): 348/350 (MH+); NMR (250 Mhz, DMSO-d6) d: 1.15 (t, 3H); 3.70 (q, 2H); 4.63 (m, 2H); 4.83 (s, 1H); 5.27 (dd, J=10 Hz, 2 Hz, 1H); 5.40 (dd, J=16 Hz, 2 Hz, 1H); 6.04 (m, 1H); 7.00 (d, J=2 Hz, 1H); 7.05 (d, J=8 Hz, 1H); 7.10 (d, J=8 Hz, 1H); 7.26 (dd, J=2 Hz, 8 Hz, 1H); 7.83 (d, J=8 Hz, 1H).

EXAMPLE 34

N-(4-Methylthiazol-5-ylsulphonyl)-6-[N-(5-bromo-2-(2-methylprop-2-en-1-yloxy)benzyl)-N-ethylamino]pyridazine-3-carboxamide The title compound was prepared from compound 15 in example 2 using a similar method to that of example 13. (Yield 54%)

M.p. 127.8° C.; MS: 566 (M+H)$^+$, 588 (M+Na)$^+$; NMR (MHz, DMSO-d$_6$) δ: 1.15 (t, 3H); 1.8 (s, 3H); 2.35 (s, 3H); 3.7 (q, 2H); 4.5 (s, 2H); 4.65 (s, 2H); 4.95 (s, 1H); 5.05 (s, 1H); 7.0 (d, 1H); 7.1 (d, 1H); 7.3 (d, 1H); 7.4 (dd, 1H); 7.8 (d, 1H); 9.25 (s, 1H). Elemental Analysis: $C_{22}H_{24}BrN_5O_4S_2$; Calc: % C, 46.6; H, 4.27; N, 12.4; Found: % C,46.5; H, 4.3; N, 12.5;

EXAMPLE 35

5-[6-(N-[5-Bromo-2-(2-methylprop-2-en-1-yloxy) benzyl]-N-ethylamino)pyridazin-3-yl]-2-thioxo-2,3-dihydro-1,3,4-oxadiazole 6-[N-(5-Bromo-2-(2-methylprop-2-en-1-yloxy)benzyl)-N-ethylamino]pyridazine-3-carbohydrazide (reference example 26) (750 mg, 1.78 mmol) was dissolved in THF (25 ml) and triethylamine (0.57 ml, 3.91 mmol) added followed by thiophosgene (0.1 ml, 1.96 mmol). The solution was stirred at ambient temperature under argon for 3 hours, then the THF removed in vacuo, water (75 ml) added, and then acetic acid was added dropwise till the mixture was at pH 5. The mixture was extracted with ethyl acetate(3×200 ml) and the combined organic phases washed with water and saturated brine (100 ml of each), dried (MgSO$_4$) and concentrated in vacuo to give the title compound as a gum (1.7 g) which was purified by MPLC (98:2 dichloromethane:methanol), to give a solid foam (230 mg 28%).

MS: 462 (M+H)$^+$, 484 (M+Na)$^+$; NMR (MHz, DMSO-d$_6$) δ: 1.31 (t, 3H); 1.56 (s, 3H); 3.70 (q, 2H); 4.55 (s, 2H); 4.85 (s, 2H); 4.95 (s, 1H); 5.1(s, 1H); 7.0 (d, 1H); 7.15 (d, 1H); 7.17 (d, 1H); 7.37 (dd, 1H); 7.82 (d, 1H). Elemental Analysis: $C_{19}H_{20}BrN_5O_2S.0.5 H_2O$; Calc: % C, 48.4; H, 4.5; N, 14.9; Found: % C,48.0; H, 4.3; N, 14.6.

EXAMPLE 36

2-[6-(N-[5-Bromo-2-(2-methylprop-2-en-1-yloxy) benzyl]-N-ethylamino)pyridazin-3-yl]-1,3,4-oxadiazole 6-[N-(5-Bromo-2-(2-methylprop-2-en-1-yloxy)benzyl)-N-ethylamino]pyridazine-3-carbohydrazide (reference example 26) (750 mg, 1.78 mmol) was dissolved in triethyl orthoformate(10 ml) then stirred at 170° C. for 5 hours. The excess triethyl orthoformate was removed in vacuo and the residue purified by MPLC (98:2 dichloromethane:methanol), to give a gum (390 mg) which was triturted with ether/hexane to give the title compound as a solid (160 mg, 21%).

M.p. 90–92° C.; MS: 429 (M+H)+; NMR (MHz, DMSO-$d_6$) δ: 1.12 (t, 3H); 1.75 (s, 3H); 3.70 (q, 2H); 4.55 (s, 2H); 4.85 (s, 2H); 4.95 (s, 1H); 5.08(s, 1H); 7.0 (d, 1H); 7.15 (d, 1H); 7.23 (d, 1H); 7.42 (dd, 1H); 8.05 (d, 1H); 9.67.(s, 1H). Elemental Analysis: $C_{19}H_{20}BrN_5O_2$; Calc: % C, 53.0; H, 4.7; N, 16.3; Found: % C, 53.4; H, 4.8; N, 16.0.

EXAMPLE 37

6-[N-(5-Chloro-2-(2-methylprop-2-en-1-yloxy) benzyl)-N-ethylamino]pyridazine-3-sulphonamide A mixture of N-ethyl-5-chloro-2-(2-methylprop-2-en-1-yloxy)benzylamine (2.76 g, 10 mmol), 3-chloro-pyridazine-6-sulphonamide [Archiv der Pharmazie (1966) 299, 646–650 and EP patent no 96,004] (1.5 g, 7.8 mmol) and ethyl di-isopropylamine (10 ml, 57 mM) in DMF (50 ml) was stirred at 130° C. for 16 hours under a reflux condenser. The solvent was evaporated at reduced pressure and the residue partitioned between dichloromethane (100 ml) and water (100 ml). The organic layer was separated, dried over anhydrous magnesium sulphate, filtered and evaporated to give a brown gum (2.5 g). The brown gum was purified by chromatography on silica, eluting with a gradient of 0→20% ethyl acetate in dichloromethane to give the title compound as a yellow solid (600 mg).

NMR (200 MHz, DMSO-$d_6$): δ 1.17(t, J=7 Hz, 3H); 1.79(s, 3H); 3.70(q, J=7 Hz, 2H); 4.55(s, 2H); 4.97(s, 1H); 5.08(s, 1H); 7.0–7.3(m, 4H); 7.43 (s, 2H); 7.74 (d, J=8 Hz, 1H). MS (ESP+): 397/399 (1×Cl) MH+.

EXAMPLE 38

5-[6-(N-(5-Bromo-2-(2-methylprop-2-en-1-yloxy) benzyl)-N-ethylamino)pyridazin-3-yl]-3-hydroxy-2-methylpyrazole A mixture of ethyl 6-[N-(5-bromo-2-(2-methylprop-2-en-1-yloxy)benzyl)-N-ethylamino]pyridazine-3-carboxylate (reference example 29) (1.2 g, 2.5 mmol) and N-methylhydrazine (0.13 ml, 2.5 mmol) in ethanol (25 ml) was refluxed for 16 hours. The solvent was evaporated at reduced pressure, the residue partitioned between dichloromethane and 1N HCl (50 ml each) and the organic layer separated and dried over anhydrous magnesium sulphate. The product was purified by chromatography on silica, eluting with methanol (10%) in dichloromethane and by crystallisation from ethyl acetate to give a white powder (500 mg) m.p. 151–2° C.

MS (ESP+): 458/460 (M+H)+(1×Br); Analysis: Calc % C, 55.0; H, 5.3; N, 15.3. Found C, 54.6; H, 5.1; N, 15.1; NMR (200 MHz, DMSO-$d_6$) δ 1.15 (t, J=7 Hz, 3H); 1.80 (s, 3H); 3.58 (s, 3H); 3.65(q, J=7 Hz, 2H); 4.55(s, 2H); 4.78(s, 2H); 4.98(s, 1H); 5.1(s, 1H); 5.90 (s, 1H); 6.98(d, J=8 Hz, 1H); 7.1(m, 2H); 7.37(dd, J=2, 8 Hz, 1H); 7.77 (broad d, J=8 Hz, 1H); 11.05(broad s, 1H).

Reference Example 1

Methyl 2-[N-(5-bromo-2-(2-chloroallyloxy)benzyl)-N-ethylamino]-5-pyridyl-carboxylate A solution of methyl 2-[N-(5-bromo-2-hydroxybenzyl)-N-ethylamino]-5-pyridylcarboxylate (reference example 7) (0.73 g, 2 mM) in DMF (12 ml) was treated with $K_2CO_3$ (0.83 g, 6 mM) and 2,3-dichloro-1-propene (0.490 g, 44 mM). The reaction was allowed to stir at ambient temperature for 48 hours. The reaction was evaporated at reduced pressure. The residue was subjected to chromatography (eluant: ethyl acetate/hexane) to give the title compound as a white solid (0.8 g).

MS (CI+): 439 (M+H)+; NMR (200 MHz, CDCl): δ 1.23 (t, 3H); 3.63 (q, 2H); 3.87 (s, 3H); 4.62 (s, 2H); 4.80 (s, 2H); 5.47 (m, 1H); 5.55 (m, 1H); 6.45 (d, 1H); 6.75 (d, 1H); 7.17 (d, 1H); 7.32 (dd, 1H); 8.0 (dd, 1H); 8.82 (d, 1H).

Reference Example 2

The compounds in the following table were prepared using a similar method to that of Reference Example 1 using the appropriate alkylating agent (in which X is the leaving group).

| D | X | Footnote |
|---|---|---|
| —CH(Me)CH=CH$_2$ | Cl | a |
| —CH$_2$CH=CHMe | Cl | b |
| —CH$_2$C(Me)=CH$_2$ | Cl | c |
| —CH$_2$CH$_2$CH=C(Me)$_2$ | Br | |
| —CH$_2$CH=C(Me)$_2$ | Br | |
| —CH$_2$CH$_2$CH=CH$_2$ | Br | |
| —CH$_2$-cyclohex-2-enyl | Br | d |
| —CH$_2$C(Cl)=CHCl(Z) | Cl | e |
| —CH$_2$C(Cl)=CHCl (E:Z-85:15) | Cl | e,f |

Footnotes
a: NMR(250MHz, CDCl$_3$): δ1.22(t, J=7Hz, 3H); 1.45(d, J=6Hz, 3H); 3.64 (q, J=7Hz, 2H); 3.87(s, 3H); 4.76(m, 3H); 5.21(m, 2H); 5.9(m 1H); 6.4(d, J=8Hz, 1H); 6.75 (dd, J=3, 8Hz, 1H); 7.14(m, 1H); 7.28(m, 1H); 7.95(m, 1H); 8.8(d, J=3Hz, 1H).
b: NMR(250MHz, CDCl$_3$): δ1.22(t, J=7Hz, 3H); 1.75(m, 3H); 3.64(q, J=7Hz, 2H); 3.87(s, 3H); [4.57(m) and 4.63(m) together 2H]; 4.74(s, 2H); 5.77(m, 2H); 6.40(d, J=8Hz, 1H); 6.75(m, 1H); 7.13(m, 1H); 7.28(m, 1H); 7.95(dd, J=2, 8Hz, 1H); 8.82(d, J=2Hz, 1H).
c: MS(CI+): 414(M+H)+ NMR(200MHz, DMSO-d$_6$): δ1.13(t, J=7Hz, 3H); 1.79(s, 3H); 3.63(q, J=7H, 2H); 3.8(s, 3H); 4.54(s, 2H); 4.97(s, 1H); 5.1 (bs, 1H); 6.68(d, J=9Hz, 1H); 7.0(d, J=8Hz, 1H); 7.05(d, J=3Hz, 1H); 7.38 (dd, J=9Hz, 1H); 7.38(dd, J=9Hz, 3Hz); 7.75(dd, J=3, 9Hz, 1H); 8.63(d, J=3Hz, 1H).
d: MS(FAB+): 445(M+H)+ NMR(200MHz, DMSO-d$_6$): δ1.1(t, J=7Hz, 3H); 1.8(m, 6H); 3.58; (q, J=7Hz, 2H); 3.78(s, 3H); 4.7(s, 2H); 4.93(m, 1H); 5.9(m, 2H); 6.65(d, J=7Hz, 1H); 7.07(m, 2H); 7.48(dd, J=2, 9Hz, 1H); 7.92(dd, J=2, 9Hz, 1H); 8.62(d, J=2Hz, 1H).
e: NMR(250MHz, DMSO-d$_6$): δ1.12(t, J=7Hz, 3H); 3.60(q, J=7Hz, 2H); 375(s, 3H); 4.75(s, 2H); 4.96(s, 2H); 6.67(d, J=9Hz, 1H); 7.00(s, 1H); 7.05(d, J=8Hz, 1H); 7.1(d, J=3Hz, 1H); 7.44(dd, J=3Hz, 8Hz, 1H); 7.93 (dd, J=3Hz, 8Hz, 1H); 8.64(d, J=3Hz, 1H).
f: NMR(250MHz, DMSO-d$_6$, E isomer): δ1.12(J=7Hz, 3H); 3.6(q, J=7Hz, 2H); 3.76(s, 3H); 4.75(s, 2H); 4.90(s, 1.6H); 6.66(d, J=9Hz, 1H); 7.08(m, 2H); 7.25(s, 0.8H); 7.42(dd, J=3Hz, 8Hz, 1H); 7.93(dd, J=3H, 8Hz); 8.63 (d, J=3Hz, 1H).

Reference Example 3

Methyl 2-[N-(5-bromo-2-(2-methylbut-2-en-1-yloxy)benzyl-N-ethylamino]-5-pyridylcarboxylate A solution of the methyl 2-[N-(5-bromo-2-hydroxybenzyl)-N-ethylamino]-5-pyridylcarboxylate (reference example 7) (0.4 g, 1.1 mmol) in THF (10 ml) under argon was treated with triphenylphosphine (0.32 g, 1.2 mmol) and diethylazodicarboxylate (0.34 ml, 0.38 g, 2.2 mmol). A solution of 2-methylbut-2-en-1-ol (0.14 g, 1.6 mmol) in THF (2 ml) was added. The reaction was stirred at ambient temperature for 60 hours. The reaction was evaporated and the residue was taken up in ethyl acetate and washed with water. The aqueous layer was extracted with ethyl acetate twice. The organic phases were combined, dried (MgSO$_4$) and evaporated. The residue was subjected to chromatography (eluant: ethyl acetate) to give the title compound as a pale yellow oil (0.22 g, 45%).

MS (CI$^+$): 433 (M+H)$^+$; NMR (250 MHz, DMSO-d$_6$): δ 1.15 (t, J=7 Hz, 3H); 1.63 (d, J=7 Hz, 3H); 1.68 (s, 3H); 3.6 (q, J=7 Hz, 2H); 3.79 (s, 3H); 4.46 (s, 2H); 4.75 (s, 2H); 5.69 (m, 1H); 6.65 (d, J=9 Hz, 1H); 6.97 (d, J=9 Hz, 1H); 7.03 (cd, J=2 Hz, 1H); 7.35 (dd, J=2, 9 Hz, 1H); 7.93 (dd, J=2,9 Hz, 1H); 8.63 (d, J=2 Hz, 1H).

Reference Example 4

The compounds in the following table were prepared using a similar method to that of Reference Example 3 using the appropriate alcohol as starting material.

| Z | D | MS | C$_{1-3}$alkyl | Footnote |
|---|---|---|---|---|
| CH | ![3-methylcyclohex-2-enyl] CH$_3$ | (FAB$^+$)459(M+H)$^+$ | Me | a) |
| CH | ![dimethylcyclohexenyl] CH$_3$, H$_3$C, CH$_3$ | (CI$^+$)487(M+H)$^+$ | Me | b) |
| CH | ![isopropenyl-methylcyclohexenyl] H$_3$C, =CH$_2$, H$_3$C | (CI$^+$)499(M+H)$^+$ | Me | c) |
| N | —CH$_2$C(Me)=CH$_2$ | | Et | d) |
| N | —CH$_2$C(Me)=CH$_2$ | | Bu | e) | a) NMR(250MHz, DMSO-d$_6$): δ1.1(t, J=7Hz, 3H); 1.63(d, J=7Hz, 3H); 1.68(s, 3H); 3.6(q, J=7Hz, 2H); 3.79(s, 3H); 4.46(s, 2H); 4.75(s, 2H); 5.69 (m, 1H); 6.65(s, J=9Hz, 1H); 6.97(d, J=9Hz, 1H); 7.03(s, J=2Hz, 1H); 7.35(dd, J=2, 9Hz, 1H); 7.93(dd, J=2, 9Hz, 1H); 8.63(d, J=2Hz, 1H).
b) NMR(250MHz, DMSO-d$_6$): δ0.95(s, 3H); 1.0(s, 3H); 1.10(t, J=7Hz, 3H); 1.42(m, 1H); 1.67(s, 3H); 1.78(m, 3H); 3.56(q, J=7Hz, 2H); 3.79(s, 3H); 4.68(s, 2H); 4.93(bs, 1H); 5.5(s, 1H); 6.64(d, J=9Hz, 1H); 7.05(m, 2H); 7.47(dd, J=2, 9Hz, 1H); 7.92(dd, J=2, 9Hz, 1H); 8.63(d, J=2Hz, 1H).
c) NMR(250MHz, DMSO-d$_6$): δ1.09(t, J=7Hz, 3H); 1.48(m, 1H); 1.7(m, 6H); 1.8–2.4(m, 4H); 3.56(q, J=7Hz, 2H); 3.79(s, 3H); 4.77(m, 4H); 5.14 (m, 1H); 5.7(m, 1H); 6.69(d, J=9Hz, 1H); 7.15(m, 2H); 7.44(m, 1H); 7.94 (m, 1H); 8.65(m, 1H).
d) MS(ESP+): 434(M+H)$^+$ NMR(250MHz, DMSO-d$_6$)δ: 1.16(t, J=7Hz, 3H); 1.32(t, J=7Hz, 3H); 1.78(s, 3H); 3.7(q, J=7Hz, 2H); 4.33(q, J=7Hz, 2H); 4.55(s, 2H); 4.85(s, 2H); 4.98(s, 1H); 5.07(s, 1H); 6.99(d, J=8Hz, 1H); 7.1(m, 2H); 7.39(dd, J=3,9Hz, 1H); 7.43(d, J=8Hz, 1H).
e) starting material prepared in reference example 11.

Reference Example 5

4-Hydroxy-3-methylbut-2-ene

To a suspension of lithium aluminium hydride, (0.47 g, 12.4 mM) in THF (30 ml) at 0° C. was added to a solution of tiglic acid (1.0 g, 10 mM) in THF (20 ml). The reaction was allowed to warm to ambient temperature and stirred overnight. The reaction was quenched by the addition of dilute hydrochloric acid and extracted with ethyl acetate three times. 4-Hydroxy-3-methylbut-2-ene thus obtained was used without purification in the subsequent step (0.29 g, 30%).

MS (EI$^+$): 86 (M+); NMR (250 MHz, DMSO-d$_6$): δ 1.55 (m, 6H); 3.8 (bs, 2H); 4.55 (bs, 1H).

Reference Example 6

Methyl 2-[N-(2-allyloxy-5-bromobenzyl)-N-ethylamino]-5-pyridylcarboxylate

A solution of 5-bromo-salicaldehyde (20.1 g, 100 mM) in DMF (50 ml) was treated with potassium carbonate (20.7 g, 150 mM) and allyl bromide (12.7 g, 10.5 mM).

The reaction was stirred at ambient temperature for 18 hours. The reaction was partitioned between ethyl acetate/water. The organic phase was washed with water four times, dried (MgSO$_4$) and evaporated at reduced pressure to give 2-allyloxy-5-bromobenzoic acid as a pale yellow oil (10.0 g, 41%).

MS (CI+): 241 (M+H)$^+$; NMR (200 MHz, DMSO-d$_6$): δ 4.74 (M, 2H); 5.37 (m, 2H); 6.1 (m, 1H); 7.20 (d, J=9 Hz, 1H); 7.76 (m, 2H); 10.3 (s, 1H).

A solution of 2-allyloxy-5-bromobenzaldehyde (5.27 g, 21.9 mM) was treated with sodium borohydride, (0.415 g, 10.9 mM). The reaction was stirred at ambient temperature for 2½ hours, water was added and the solvent removed at reduced pressure. The residue was acidified to pH 1 and extracted with ethyl acetate twice. The organic layers were combined, dried (MgSO$_4$) and evaporated to give 2-allyloxy-5-bromobenzyl alcohol (5.12 g, 96%) as a white solid.

MS (EI+): 242 (M+); NMR: (250 MHz, DMSO-d$_6$): δ 4.5 (s, 2H); 4.55 (me, 2H); 5.15 (bs, 1H); 5.3 (m, 2H); 6.02 (m, 1H); 6.9 (d, J=9 Hz, 1H); 7.35 (dd, J=2 Hz, 9 Hz, 1H); 7.47 (d, J=2 Hz, 1H).

A solution of 2-allyloxy-5-bromobenzyl alchohol (5.12 g, 21.1 mM) in dichloromethane (25 ml) was treated with triphenylphosphine (6.15 g, 23.5 mM) and carbon tetrabromide (8.67 g, 26.13 mM). The reaction was stirred at ambient temperature overnight. The solvent was evaporated at reduced pressure and 2-allyloxy-5-bromobenzylbromide, thus obtained, used in the subsequent step without purification.

Sodium hydride (60%, 0.909 g, 22.7 mM) was washed with hexane three times and suspended in DMF (10 ml). A solution of methyl 2-ethylamino-5-pyridylcarboxylate (4.02 g, 22.3 mM) was added dropwise and the reaction was allowed to stir at ambient temperature for 1 hour. A solution of 2-allyloxy-5-bromobenzylbromide (21.1) was added and the reaction was stirred for 23 hours at ambient temperature. The reaction was quenched with water and extracted with ethyl acetate. The organic layer was washed with water three times, dried (MgSO$_4$) and evaporated. Chromatography (eluant: ethyl acetate/hexane) gave methyl 2-[N-(2-allyloxy-5-bromobenzyl)-N-ethylamino]-5-pyridylcarboxylate as a dark yellow oil which was used in the next stage without further purfication.

Reference Example 7

Methyl 2-[N-(5-bromo-2-hydroxybenzyl)-N-ethylamino]pyridine-5-carboxylate

6-Chloronicotinic acid (100 g, 0.63 mol) was treated with ethylamine (70% in water, 500 ml). The reaction was sealed in an autoclave and heated to 170° C. for 6 hours. The reaction mixture was evaporated, partially neutralised with concentrated HCl and the pH adjusted to pH5 with glacial acetic acid. The solid product was filtered off and dried in vacuo for 18 hours to give 6-(ethylamino)nicotinic acid (87.8 g, 84%).

MS (CI$^+$)=167 (M+H)$^+$; NMR (250 MHz, DMSO-d$_6$) δ: 1.15 (t, J=7 Hz, 3H); 3.3 (q, J=7 Hz, 2H); 6.45 (d, J=9 Hz, 1H); 7.25 (brt, 1H); 7.78 (dd, J=2, 9 Hz, 1H); 8.54 (d, J=2 Hz, 1H); 11.6 (brs, 1H).

A suspension of 6-(ethylamino)nicotinic acid (50 g, 0.3 mol) in methanol (500 ml) was treated with concentrated H$_2$SO$_4$ (30 ml). The reaction was heated at reflux for 18 hours. The reaction mixture was then evaporated, poured into ice water (1 L) and adjusted to pH8 with solid sodium hydrogen carbonate (foaming). The aqueous mixture was extracted with ethyl acetate (3×300 ml) and the organic layers combined, dried (MgSO$_4$) and evaporated to give methyl 6-(ethylamino)nicotinoate as an off-white solid (45.5 g, 84%).

MS (CI+): 181 (M+H)$^+$; NMR (200 MHz, DMSO-d$_6$) δ: 1.14 (t, J=7 Hz, 3H); 3.3 (q, J=7 Hz, 2H); 3.76 (s, 3H); 6.46 (d, J=9 Hz, 1H); 7.39 (brt, 1H); 7.80 (dd, J=3, 9 Hz, 1H); 8.56 (d, J=3 Hz, 1H).

A solution of 5-bromosalicylaldehyde (12.0 g, 59.7 mmol) in DMF (50 ml) was treated with K$_2$CO$_3$ (16.5 g, 120 mmol) and benzyl bromide (11.2 g, 65.6 mmol). The reaction was stirred at ambient temperature for 18 hours, diluted with ethyl acetate and filtered. The filtrate was washed with HCl (0.05 M), saturated aqueous sodium hydrogen carbonate and brine. The organic phase was dried (Na$_2$SO$_4$) and evaporated and the residue triturated with hexane/ethyl ether. The product was filtered off to give 2-benzyloxy-5-bromobenzaldehyde as a white solid (15.8 g, 90%) m.p. 70–72° C.

MS (CI+): 291 (M+H)$^+$; NMR (200 MHz, DMSO-d$_6$) δ: 5.38 (s, 2H); 7.5 (m, 6H); 7.9 (m, 2H); 10.41 (s, 1H).

A suspension of 2-benzyloxy-5-bromobenzaldehyde (14.5 g, 50.2 mmol) in absolute ethanol (250 ml) was treated with sodium borohydride (2.6 g, 68.8 mmol). The reaction was stirred and the temperature slowly rose to 33° C. After 1 hour the reaction mixture was evaporated and the residue dissolved in ethyl acetate and poured into a mixture of ice water (200 ml) and 1N HCl (25 ml). The organic layer was separated, washed with aqueous sodium hydrogen carbonate, brine, dried (Na$_2$SO$_4$) and evaporated to give 2-benzyloxy-5-bromobenzylalcohol as a pale yellow oil (14.85 g, quantitative).

MS (CI+) 292 (M+); NMR (200 MHz, DMSO-d$_6$) δ: 4.52 (d, J=5 Hz, 2H); 5.12 (s, 2H); 5.17 (t, J=5 Hz, 1H); 6.98 (d, J=9 Hz, 1H); 7.4 (m, 6H); 7.5 (d, 2H, 1H).

A solution of 2-benzyloxy-5-bromobenzyl alcohol (14.75 g, 50.2 mmol) in anhydrous ethyl ether (150 ml) was cooled to 4° C. A solution of PBr$_3$ (13.68 g, 50 mmol) in anhydrous ether (40 ml) was added dropwise keeping the temperature below 10° C. The reaction was allowed to warm to ambient temperature and stirred for 1 hour. The reaction was filtered through silica gel (200 g). The silica gel was washed with ethyl ether to remove all the product. The filtrate was washed with water (1×150 ml), aqueous saturated sodium hydrogen carbonate (1×150 ml) and brine (1×150 ml). The organic layer was dried (Na$_2$SO$_4$) and evaporated to give 2-benzyloxy-5-bromobenzylbromide as a pale yellow oil (15.2 g, 85%) which crystallised on standing.

MS (EI+): 354 (M+); NMR (200 MHz, DMSO-d$_6$): δ 8:4.65 (s, 2H); 5.2 (s, 2H); 7.05 (d, J=9 Hz, 1H), 7.4 (m, 6H); 7.66 (d, J=3 Hz, 1H).

A solution of methyl 6-ethylaminonicotinoate (152 g, 84.4 mmol) in DMF (50 ml) was cooled to 0° C. and treated with sodium hydride (60%. 75 mmol). The reaction was stirred for 1 hour and a solution of 2-benzyloxy-5-bromobenzylbromide (25 g, 70.2 mmol) in DMF (50 ml) added. The reaction was allowed to warm to ambient temperature and stirred for 18 hours. The reaction was quenched with water and extracted with ethyl acetate (three times). The organic layers were combined, washed with water and brine twice, dried (MgSO$_4$) and evaporated to give a white solid. Recrystallisation from ethyl/acetate/hexane gave methyl 2-[N-(2-benzyloxy-5-bromobenzyl)-N-ethylamino]pyridine-5-carboxylate (22.7 g, 71%).

MS (CI+): 455/457 (M+H)$^+$; NMR (200 MHz, DMSO-d$_6$) δ: 1.1 (t, J=7 Hz, 3H); 3.5 (q, J=7 Hz, 2H); 3.78 (s, 3H); 4.77 (s, 2H); 5.18 (s, 2H); 6.65 (d, J=9 Hz, 1H); 7.08 (m, 2H); 7.4 (m, 6H); 7.9 (dd, J=2, 9 Hz, 1H); 8.62 (d, 1H).

A solution of methyl 2-[N-(2-benzyloxy-5-bromobenzyl)-N-ethylamino]-5-pyridylcarboxylate (10.0 g, 22 mM) in dichloromethane (150 ml) was treated with boron trichloride dimethyl sulfide complex (40 ml, 2M, 80 mM). The reaction was stirred at ambient temperature for 48 hours. Saturated sodium bicarbonate solution was added and the layers were separated. The aqueous layer was washed with dichloromethane. The organic layers were combined, dried ($MgSO_4$) and evaporated to give an off-white solid. The off-white solid was subjected to chromatography (diluted with ethyl acetate/hexane) to give the title compound (6.02 g, 75%).

MS (CI+) 365 (M+H)+; NMR (250 MHz, DMSO-$d_6$): δ 1.14 (t, J=7 Hz, 3H); 3.61 (q, J=7 Hz, 2H); 3.78 (s, 3H); 4.66 (s, 2H); 6.65 (d, J=9 Hz, 1H); 6.8 (d, J=9 Hz, 1H); 7.02 (d, J=2 Hz, 1H); 7.2 (dd, J=2, 9 Hz, 1H); 7.93 (dd, J=2, 9 Hz, 1H); 8.64 (d, J=2 Hz, 1H); 10.13 (s, 1H).

Reference Example 8

2-[N-(5-Bromo2-(2-chloroprop-2-en-1-yloxy) benzyl)-N-ethylamino]-5-cyanopyridine 2-[N-(5-Bromo-2-hydroxybenzyl)-N-ethylamino] pyridine-5-carboxamide (example 4) (1.0 g, 2.85 mmol) was suspended in tetrahydrofuran (15 ml) and the stirred solution treated with pyridine (0.46 ml, 0.46 g, 5.7 mmol) and trifluoroacetic anhydride (0.9 ml, 1.35 g, 6.4 mmol) at ambient temperature (slight exotherm). A yellow colour became apparent and the solid dissolved in the THF. The solution was left standing at ambient temperature overnight, then further pyridine (0.46 ml, 5.7 mmol) and TFAA (0.90 ml, 6.4 mmol) were added and the reaction was again left overnight. The mixture was evaporated to low volume, saturated sodium bicarbonate solution was added and the mixture stirred at ambient temperature for 30 minutes, evaporated to low volume and the resultant white precipitate filtered, washed with water and air dried to give 2-[N-(5-bromo-2-hydroxybenzyl)-N-ethylamino]-5-cyanopyridine as a white solid (1.0 g, 100%).

MS (CI+): 332, 334 (M+H)$^+$.

The cyano compound from the previous step (0.52 g, 1.56 mmol), in dimethyl acetamide (10 ml) was reacted with potassium carbonate (650 mg, 4.7 mmol) followed by 2,3-dichloro-1-propene (0.32 ml, 384 mg, 3.47 mmol). The mixture was stirred at ambient temperature overnight was evaporated to dryness and the residue preabsorbed to silica (1.5 g) and purified by MPLC to give the title compound as a white gum (0.4 g, 63%).

MS (ESP+): 406, 408 (M+H)$^+$.

Reference Example 9 n-Butyl 6-[N-(5-bromo-2-(2-chloroprop-2-en-1-yloxy)benzyl)-N-ethylamino]-pyridazine-3-carboxylate n-Butyl 6-[N-(5-bromo-2-hydroxybenzyl)-N-ethylamino] pyridazine-3-carboxylate (reference example 11) (0.28 g, 0.69 mmol) in DMF (4 ml) was treated with potassium carbonate (2.05 mmol) followed by 2,3-dichloroprop-1-ene (168 mg, 140 μl, 1.4 mmol) and the reaction stirred at ambient temperature over the weekend. The reaction mixture was evaporated to dryness, preabsorbed onto silica (1.5 g) and purified by MPLC to give the title compound as a colourless gum (0.24 g, 72%).

MS (CI+): 482, 484 (M+H)$^+$.

Reference Example 10

2-[N-(5-Bromo-2-(2-methylprop-2-en-1-yloxy) benzyl)-N-ethylamino]-5-cyano pyridine 2-[N-(5-Bromo-2-hydroxybenzyl)-N-ethylamino] pyridine-5-carboxamide (example 4) (1.93 g, 5.5 mmol) was suspended in THF (30 ml) and treated with pyridine (1.15 g, 14.25 mmol, 1.15 ml) followed by trifluoroacetic anhydride (3.4 g, 16 mmol) whilst stirring at ambient temperature. The white solid dissolved and there was a slight exotherm. The resultant solution was left overnight at ambient temperature. The mixture was then evaporated to low volume, a saturated aqueous solution of sodium bicarbonate was added and the mixture stirred at ambient temperature for 30 minutes. The mixture was again evaporated to low volume and the white solid that precipitated was filtered, washed with water and sucked dry (1.68 g). The solid was purified by MPLC on silica to give 2-[N-(5-bromo-2-hydroxybenzyl)-N-ethylamino]-5-cyanopyridine as a white solid (1.15 g, 63%).

MS (CI+): 332, 334 (M+H)$^+$.

The cyano compound from the previous step (0.52 g, 1.56 mmol) in dimethylacetamide (10 ml) was treated with potassium carbonate (0.65 g, 4.7 mmol) followed by 3-chloro-2-methylpro-1-ene and stirred for 48 hours at ambient temperature. The mixture was evaporated to dryness and the residue applied directly to silica and purified by MPLC to give 2-[N-(5-bromo-2-(2-methylprop-2-en-1-yloxy)benzyl)-N-ethylamino]-5-cyanopyridine (0.45 g, 75%) which was subsequently crystallised.

MS (ESP+): 386, 388 (M+H)$^+$. NMR (200 MHz, DMSO-$d_6$) δ: 1.15 (t, 3H); 1.76 (bs, 3H); 3.68 (bq, 2H); 4.53 (s, 2H); 4.85; (s, 2H); 4,97 (s, 1H); 5.06 (s, 1H); 7.0 (d, 1H); 7.18 (m, 2H); 7.4 (dd, 1H); 7.83 (1H).

Reference Example 11

Butyl 6-[N-(5-bromo-2-hydroxybenzyl)-N-ethylamino]pyridazine-3-carboxylate

A suspension of 6-chloropyridazine-3-carboxamide (reference example 13, paragraphs 1 to 3) (28.5 g, 0.18 mol) in methanol (200 ml) was treated with aqueous ethylamine (70% solution, 77 ml). The reaction was heated at reflux for 3½ hours. The reaction was allowed to cool to ambient temperature and stand overnight. The precipitate was filtered and washed with a small volume of water and dried to give 6-(ethylamino)pyridazine-3-carboxamide as pink solid (8.9 g). [The filtrates were evaporated to a small volume diluted with cold water (100 ml) and more of the desired solid was filtered-off, washed with water and dried (12.8 g). Total yield (21.7 g, 72%)].

A solution of 6-(ethylamino)pyridazine-3-carboxamide (21.7 g, 0.131 mol) in n-butanol (109 ml) and $BF_3.Et_2O$ (54 ml) was heated under an air condenser (allowing evaporation of $Et_2O$) at 120° C. for 18 hours. The reaction was evaporated at reduced pressure and the residue dissolved in ice/water (400 ml) and neutralized with stirring using solid sodium bicarbonate. The oily precipitate was extracted with dichloromethane (250 ml) containing methanol (50 ml). The extracts were dried ($MgSO_4$) and evaporated (in vacuo) to give a slightly sticky solid which was recrystallised from ethyl acetate (~250 ml) to give butyl 6-(ethylamino) pyridazine-3-carboxylate as an off-white solid (22.0 g, 75%).

A suspension of the butyl ester from the previous step (21 g, 0.094 mol) in acetic acid (400 ml) was treated with 4-bromophenol (65.5 g, 0.378 mol) and paraformaldehyde (3.15 g, 0.105 mol). The reaction was heated at 100° C. for 4.5 hours and a further portion of paraformaldehyde (6.3 g, 0.21 mol) added and the reaction heated at 100° C. for 16 hours. The resulting dark coloured reaction was evaporated to give a dark oil. Chromatography (eluant: diethyl ether/hexane) gave fast running materials as a brown oil. This oil was dissolved in ethyl acetate (~70 ml) and allowed to stand overnight at ambient temperature to give a. white solid precipitated, which was filtered and washed with ethyl acetate and dried to give butyl 6-[N-(5-bromo-2-hydroxybenzyl)-N-ethylamino]pyridazine-3-carboxylate as the product (12.3 g, 32%).

Reference Example 12

Butyl 6-[N-(5-bromo-2-(2-chloroprop-2-en-1-yloxy) benzyl)-N-ethylamino]pyridazine-3-carboxylate Butyl 6-[N-(5-bromo-2-hydroxybenzyl)-N-ethylamino] pyridazine-3-carboxylate (reference example 11) (0.28 g, 0.69 mmol) in DMF (4 ml) was treated with potassium carbonate (0.28 g, 2.05 mmol) followed by 2,3-dichloro-1-propene (168 mg, 140 μl, 1.4 mmol) and the mixture stirred at ambient temperature over the weekend. The mixture was evaporated, in vacuo, to dryness, presorbed to 1.5 g silica and purified by MPLC to give the title compound as a colourless gum (0.24 g, 72%).

MS (CI+): 482, 484 (M+H)$^+$.

Reference Example 13

6-[N-(5-Bromo-2-(2-methylprop-2-en-1-yloxy) benzyl)-N-ethylamino]-3-cyanopyridazine 1. A mixture of 6-oxo-1,6-dihydropyridazine-3-carboxylic acid (117.24 g) [Ref: British Patent 856, 409], n-butyl acetate (293 ml), n-butanol (410 ml) and conc. $H_2SO_4$ (5.9 ml) was heated at reflux for 1 hour. The solvent was evaporated and the residue washed with n-butyl acetate to give n-butyl 6-oxo-1,6-dihydropyridazine-3-carboxylate (130.6 g, 79.6% yield), mpt 79–80° C.

NMR (DMSO-d$_6$) δ: 0.93 (t, 3H, J=7.5 Hz), 1.40 (sextet, 2H, J=7.5 Hz), 1.67 (m, 2H), 4.28 (t, 2H, J=6.5 Hz), 6.96 (d, 1H, J=10 Hz), 7.83 (d, 1H, J=10 Hz), 13.56 (broad s, 1H).

2. To a mixture of phosphorus oxychloride (20 ml) and acetonitrile (40 ml) heated at reflux was added a solution of n-butyl 6-oxo-1,6-dihydropyridazine-3-carboxylate (20 g) in acetonitrile (80 ml). The reaction was heated at reflux for 30 minutes, cooled and added to an ice cooled solution of $K_2CO_3$ (87.8 g) in water (600 ml) with vigorous stirring. The product was filtered off, washed with water and dried at 60° C. to give n-butyl 6-chloropyridazine-3-carboxylate (17.5 g, 80% yield), mpt 110–111° C.

NMR (CDCl$_3$) δ: 0.99 (t, 3H, J=7.5 Hz), 1.48 (sextet, 2H, J=7.5 Hz), 1.84 (m, 2H), 4.49 (t, 2H, J=6.5 Hz), 7.71 (d, 1H, J=8.3 Hz), 8.18 (d, 1H, J=8.3 Hz).

3. Excess gaseous ammonia was added to an ice bath cooled solution of n-butyl 6-chloropyridazine-3-carboxylate (40 g) in methanol (280 ml). The mixture was stirred at ambient temperature for 4 hours and the resulting residue filtered off, washed with methanol (20 ml) and dried to give 6-chloropyridazine-3-carboxamide (28.05 g, 95.5% yield), mpt. 243–5° C.

NMR (DMSO-d$_6$) δ: 7.96 (broad, 1H), 8.07 (d, 1H, J=8.3 Hz), 8.22 (d, 1H, J=8.3 Hz), 8.52 (broad s, 1H).

4. Benzyl bromide (71.4 ml) was added dropwise to a mixture of 5-bromo-2-hydroxybenzaldehyde (100.5 g) and $K_2CO_3$ (207.5 g) in 1-methyl-2-pyrrolidinone (500 ml) at 30° C. over 1 hour. The mixture was stirred for 3 hours at 35–40° C. A solution of ethylamine hydrochloride (57.1 g) in methanol (250 ml) was added over 30 minutes at 35° C. and the mixture stirred for 3 hours at 35–40° C. A solution of sodium borohydride (26.5 g) in 1-methyl-2-pyrrolidinone (300 ml) was added over 2 hours at 35–40° C. and the mixture stirred at 40–45° C. for 2 hours. The mixture was cooled (10° C.), diluted with ethyl acetate (200 ml) and acidified with 2N HCl (3,500 ml). The resulting precipitate was filtered off, washed with toluene and 40–60 petroleum ether and dried under vacuum at 60° C. The residue was purified by stirring in a mixture of acetonitrile (140 ml) and toluene (700 ml) at 80° C. for 30 minutes, cooling to 10° C. and filtering off the product to give N-ethyl N-(2-benzyloxy-5-bromobenzyl)amine hydrochloride salt (13.6 g, 76.7% yield).

NMR (DMSO-d$_6$) δ: 1.20 (t, 3H, J=7.3 Hz), 2.97 (q, 2H, J=7.3 Hz), 4.13 (s, 2H), 5.20 (s, 2H), 7.15 (d, 1H, J=8.3 Hz), 7.22–7.60 (m, 6H), 7.70 (d, 1H, J=2.5 Hz), 8.68 (broad, s, 1H).

5. A mixture of N-ethyl-N-(2-benzyloxy-5-bromobenzyl) amine hydrochloride salt (87 g), 6-chloropyridazine-3-carboxamide (35 g) and NaHCO$_3$ (41 g) in 1-methyl-2-pyrrolidinone was heated at 115° C. for 24 hours, cooled to 20° C. and added to water (1100 ml) with vigorous stirring, maintaining the temperature below 30° C. with external cooling. Ethyl acetate (725 ml) was added and the mixture stirred at 20° C. for 2 hours. The precipitate was filtered, dried, washed with 40–60 petroleum ether and dried under vacuum at 65° C. to give 6-[N-(2-benzyloxy-5-bromobenzyl)-N-ethylamino]pyridazine-3-carboxamide (83 g, 84.7% yield), mpt. 171–172° C.

NMR (DMSO-d$_6$) δ: 1.12 (t, 3H, J=7.0Hz), 3.66 (q, 2H, J=70 Hz), 3.66 (q, 2H, J=7.0 Hz), 4.85 (s, 2H). 5.19 (s, 2H), 7.07–7.16 (m, 3H), 7.30–7.51 (m, 7H), 7.79 (d, 1H, J=9 Hz), 8.10 (broad s, 1H).

6. 6-[N-(2-Benzyloxy-5-bromobenzyl)-N-ethylamino] pyridazine-3-carboxamide (3.24 g, 7.3 mmol) in dichloromethane (50 ml) was treated with boron trichloride dimethyl sulphide reagent (18.5 ml, 2M solution) in dichloromethane (37 mmol) and the solution stirred at ambient temperature for 6 days. The mixture was carefully treated with excess aqueous sodium bicarbonate solution to give a pH of around 9. Dichloromethane was added, the organic and aqueous layers separated and the aqueous layer washed with dichloromethane. The combined organic extracts were then washed with brine, dried and evaporated to give a sticky solid. This was treated with diethylether (30 ml) and methanol (3 ml) and left at ambient temperature overnight. The resultant solid was filtered, washed with diethylether and sucked dry to give 6-[N-(5-bromo-2-hydroxybenzyl)-N-ethylamino]-pyridazine-3-carboxamide (1.34 g, 52%).

The phenol from the previous step (1.73 g, 4.9 mmol) in THF (30 ml) was treated with pyridine (0.82 ml, 0.82 g, 10.2 mmol) followed by trifluoroacetic anhydride (1.61 ml, 2.42 g, 11.5 mmol). The mixture turned dark green and was left overnight at ambient temperature. The mixture was then evaporated to a gum, treated with an excess of an aqueous solution of sodium bicarbonate and stirred at ambient temperature for approximately 30 minutes. The resultant red solid was filtered, washed with water and sucked dry (1.8 g) and purified by MPLC to give 6-[N-(5-bromo-2-hydroxybenzyl)-N-ethylamino]-3-cyanopyridazine (as a white solid (0.87 g, 53%).

MS (ESP+): 333.335 (M+H)$^+$.

The product of the previous step (0.52 g, 1.56 mmol) in dimethyl acetamide (10 ml) was treated with potassium carbonate (0.65 g, 4.7 mmol) followed by 3-chloro-2-methylpropene (340 μl, 314 mg, 3.47 mmol) and stirred at ambient temperature overnight.

The mixture was then evaporated in vacuo and the residue presorbed onto silica and purified by MPLC to give a 6-[N-(5-bromo-2-(2-methylprop-2-en-1-yloxy)benzyl)-N-ethylamino]-3-cyanopyridazine.

MS (ESP+): 387, 389 (M+H)+.

Reference Example 14

6-[N-(5-Bromo-2-(cyclohex-2-enyloxy)benzyl)-N-ethylamino]-3-cyanopyridazine

The title compound was prepared using a similar method to that of reference example 13, using 3-bromocyclohexene in place of 3-chloro-2-methylpropene to give a pale yellow gum (97%).

MS (ESP+): 413, 415 (M+H)+.

Reference Example 15

Ethyl 6-[N-(5-bromo-2-allyloxybenzyl)-N-ethylamino]pyridazin-3-carboxylic acid

The title compound was prepared from ethyl 6-[N-(5-bromo-2-hydroxybenzyl)-N-ethylamino]pyridazine-3-carboxylate (example 8) using a similar method to that of reference example 3.

NMR (250 MHz, DMSO-$d_6$) δ: 1.15 (t, 3H); 1.33 (t, 3H); 3.69 (q, 2H); 4.84 (q, 2H); 4.62 (bd, 2H); 4.84 (s, 2H); 5.27 (m, 1H); 5.91 (m, 1H); 6.04 (m, 1H); 7.00 (d, 1H); 7.1 (m, 2H); 7.4 (dd, 1H); 7.83 (d, 1H).

Reference Example 16

N-Ethyl 5-chloro-2-(2-methylprop-2-en-1-yloxy) benzylamine

A mixture of 5-chlorosalicylaldehyde (25.0 g, 0.16 mol), anhydrous potassium carbonate (70.0 g, 0.5 mol), methallyl chloride (27.0 ml, 0.27 mol) and N-methylpyrrolidinone (250 ml) was stirred under reflux condenser at 60–70° C. for 16 hours. The mixture was cooled to 20° C. and treated cautiously with a solution of ethyl amine hydrochloride (40.0 g, 0.49 mol) in 200 ml methanol (frothing occurs). After complete addition the mixture was stirred for 1 hour at 20° C., then treated portionwise with sodium borohydride (4.6 g, 0.12 mol) and small aliquots (~1.0 ml) of ether to reduce frothing. The mixture was stirred for 1 hour at 20° C. and the boron-amine complex decomposed by cautious addition of 6N HCl (200 ml), cooling as necessary. The mixture was Stirred for 1 hour at 20° C., then basified with 2N NaOH to pH10 and extracted with dichloromethane (3×250 ml). The combined organic extracts were washed with water (3×250 ml), dried over anhydrous magnesium sulphate, filtered and evaporated to give a brown oil, which was dissolved in isopropanol (200 ml). Concentrated hydrochloric acid (36% w/v, 10 ml) was added with stirring and the solution cooled at 5° C. for 2 hours, white crystalline needles formed, which were filtered off, washed with isopropanol and ether to give the title compound as the hydrochloride salt (18.0 g, 41%).

m.p. 135–136° C.; MS (CI+): 240/242 (M+H)+; NMR (200 MHz, DMSO-$d_6$) δ: 1.25 (t, J=6 Hz, 3H), 1.80 (s, 3H), 2.93 (q, J=6 Hz, 2H), 4.07 (s, 2H); 4.54 (s, 2H); 4.97 (s, 1H); 5.08 (s, 1H), 7.07 (d, J=8 Hz, 1H), 7.40 (dd, J=8 Hz, J=2 Hz, 1H), 7.70 (d, J=2 Hz, 1H), 9.47 (s, 2H). Analysis: Calc % C, 56.5; H, 6.9; N, 5.1; Cl, 25.7; Found C, 56.7; H, 6.9; N, 5.0; Cl, 25.5.

Reference Example 17

Butyl 6-[N-(5-fluoro-2-(2-methylprop-2-en-1-yloxy) benzyl)-N-ethylamino]pyridazine-3-carboxylate A mixture of butyl 6-ethylaminopyridazine 3-carboxylate (described in reference example 13)(10.0 g, 44.8 mmol) and para-formaldehyde (1.7 g, 56.6 mmol) in TFA (100 ml was stirred at 50–60° C. for 1 hour until a clear solution formed. The solution was cooled to ambient temperature and treated with 4-fluorophenol (5.6 g, 50 0 mmol), stirred for 16 hours and evaporated at reduced pressure. The residue was partitioned between ice/water (200 g) and dichloromethane (200 ml), the organic layer washed with saturated sodium bicarbonate solution, dried over anhydrous magnesium sulphate and evaporated to give a yellow gum. Chromatography on silica, eluting with 10% ether in dichloromethane, gave a solid which crystallised from ether to give butyl 6-[N-(5-fluoro-2-hydroxybenzyl)-N-ethylamino]pyridazine-3-carboxylate as pale pink needles (2.2 g).

MS (ESP+): 348 (M+H)+; NMR (200 MHz, DMSO-$d_6$) δ: 0.93 (t, J=7 Hz, 3H); 1.27 (t, J=7 Hz, 3H); 1.43 (m, 2H); 1.70 (m, 2H); 3.72 (q, J=7 Hz, 2H); 4.30 (t, J=7 Hz, 2H); 4.77 (s, 2H); 6.73–7.90 (m, 3H); 7.10 (d, J=8 Hz, 1H); 7.83 (d, J=8 Hz, 1H); 9.83 (s, 1H).

The title compound was prepared from butyl 6-[N-(5-fluoro-2-hydroxybenzyl)-N-ethylamino]pyridazine-3-carboxylate using a similar method to that of reference example 1 (Yield 95%).

NMR (200 MHz, CDCl$_3$) δ 0.97(t, J=8 Hz, 3H); 1.28(t, J=7 Hz, 3H); 1.50(m, 2H); 1.80(m, 2H); 1.85(s, 3H); 3.80(q, J=6 Hz, 2H); 4.40(t, 2H); 4.45(s, 2H); 4.85(s, 2H); 5.00(s, 1H); 5.10(s, 1H); 6.67(d, J=8 Hz); 7.83(d, J=8 Hz, 1H).

Reference Example 18

Butyl 6-[N-(5-chloro-2-(cyclohexen-3-yloxy) benzyl)-N-ethylamino]pyridazine-3-carboxylate The title compound was prepared from butyl 6-[N-(5-chloro-2-hydroxybenzyl)-N-ethylamino]pyridazine-3-carboxylate (reference example 20) using a similar method to that of reference example 1, except the reaction mixture was left for 80 hours at 50° C. and the eluant used in the chromatography was 10% diethylether/dichloromethane.

MS (ESP+): 444/446 (M+H)+; NMR (200 MHz, DMSO-$d_6$) δ: 0.98 (t, 3H); 1.15 (t, 3H); 1.45 (m, 2H); 1.70 (m, 5H); 1.90 (m, 1H); 2.04 (m, 2H); 3.66 (q, 2H); 4.30 (t, 2H); 4.77 (s, 2H); 4.93 (br s, 1H); 5.83 (dd, 1H); 5.95 (dt, 1H); 7.05 (d, 1H); 7.08 (d, 1H); 7.13 (d, 1H); 7.26 (dd, 1H); 7.82 (d, 1H).

Reference Example 19

6-[N-(5-Chloro-2-(2-methylprop-2-en-1-yloxy) benzyl)-N-ethylamino]-3-cyanopyridazine To a solution of 6-[N-(5-chloro-2-(2-methylprop-2-en-1-yloxy)benzyl)-N-ethylamino]-pyridazine-3-carboxamide (example 18) (210 mg, 0.6 mmol) in pyridine (10 ml) at 0° C. was added methane sulfonyl chloride (0.5 ml, 0.6 mmol) and the mixture allowed to stir (gradually coming to an ambient temperature as the ice melts) for 60 hours. The solution was poured into 2 N hydrochloric acid (50 ml) over ice and the product extracted with diethyl ether (200 ml), washed with water (3×200 ml), dried over anhydrous magnesium sulphate and the solvent removed in vacuo to give the title compound as a brown gum (260 mg) which was used without further purification.

Reference Example 20

Butyl 6-[N-(5-Chloro-2-hydroxybenzyl)-N-ethylamino]pyridazine-3-carboxylate

The title compound was prepared from butyl 6-(ethylamino)pyridazine-3-carboxylate and 4-chlorophenol using a similar method to that of reference example 1, except 0.4 equivalents of trifluoroacetic acid were added to the reaction mixture.

NMR (250 MHz, DMSO-$d_6$) δ: 0.94(t, 3H)); 1.17(t, 3H); 1.43(m, 2H); 1.70(m, 2H); 3.7(q, 2H); 4.28(t, 2H); 4.75(s, 2H); 6.85(d, 1H); 6.97(d, 1H); 7.1(m, 2H); 7.82(d, 1H); 10.1 (bs, 1H).

Reference Example 21

N-(2-Methoxycarbonylphenyl)-6-[N-(5-chloro-2-(2-methylprop-2-en-1-yloxy)benzyl)-N-ethylamino] pyridazine-3-carboxamide The title compound was prepared from 6-[N-(5-chloro-2-(2-methylprop-2-en-1-yloxy)benzyl)-N-ethylamino] pyridazine-3-carboxylic acid (example 19) using a similar method to that ol example 11.

M.S. (ESP+): 495/497 (MH$^+$); NMR (200 MHz, DMSO-$d_6$) δ: 1.24(t, 3H); 1.78 (s, 3H); 3.73 (q, 2H); 3.90 (s, 3H); 4.55(s, 2H); 4.88(s, 2H); 4.97 (s, 1H); 5.10 (s, 1H); 6.97 (d, 1H); 7.07(d, 1H); 7.22 (m, 3H); 7.68 (td, 1H); 7.97 (d, 1H); 8.04(dd, 1H); 8.83(d, 1H).

Reference Example 22

N-(1-Methoxycarbonylyethyl)-6-[N-(5-chloro-2-(2-methylprop-2-en-1-yloxy)benzyl)-N-ethylamino] pyridazine-3-carboxamide The title compound was prepared from 6-[N-(5-chloro-2-(2-methylprop-2-enyloxy)-benzyl)-N-ethylamino] pyridazine-3-carboxylic acid (example 19) using a similar method to that of example 11, except the title compound was not purified by column chromatography.

M.S. (ESP+): 447/449 (MH+); NMR (200 MHz, DMSO-$d_6$) δ: 1.16 (t, 3H); 1.43(d, 3H); 1.78 (s, 3H); 3.65 (s, 3H); 3.71(q, 2H); 4.55(m, 1H); 4.56(s, 2H); 4.85(s, 2H); 4.97 (s, 1H); 5.08(s, 1H); 7.00(d, 1H); 7.05(d, 1H); 7.16(d, 1H); 7.26(dd, 1H); 7.82(d, 1H); 8.95(d, 1H).

Reference Example 23

N-(α-methoxycarbonylbenzyl)-6-[N-(5-chloro-2-(2-methylprop-2-en-1-yloxy)benzyl)-N-ethylamino] pyridazine-3-carboxamide The title compound was prepared from 6-[N-(5-chloro-2-(2-methylprop-2-en-1-yloxy)-benzyl)-N-ethylamino] pyridazine-3-carboxylic acid (example 19) using a similar method to that of example 11, and purified by column chromatography (eluant: 2% iPrOH in dichloromethane.

MS: (ESP+): 509/511 (MH$^+$); NMR (200 MHz, DMSO-$d_6$) δ: 1.15(t, 3H); 1.78(s, 3H); 3.67(s, 3H); 3.69(q, 2H); 4.53(s, 2H); 4.84(s, 2H); 4.97(s, 1H); 5.08(s, 1H); 5.69(d, 1H); 6.97(d, 1H); 7.04(d, H); 7.17(d, 1H); 7.25(dd 1H); 7.38(m, 5H); 7.83(d, 1H); 9.03(d, 1H).

Reference Example 24

N-Ethyl 5-chloro-2-allyloxybenzylamine

The title compound was prepared using a similar method to that of reference example 16, except that dimethylformamide was used as the solvent and allyl bromide was used as the alkylating agent instead of methallyl chloride. Also the product was isolated as the free base and not the hydrochloride salt. (14.8 g, 67%)

MS (CI+): 226/228 (MH+); NMR (250 MHz, DMSO-$d_6$) δ: 1.04 (t, 3H); 2.57 (q, 2H); 3.68 (s, 2H); 4.58 (m, 2H); 5.29 (dd, J=10 Hz, 2 Hz, 1H); 5.40 (dd, J=16 Hz, 2 Hz, 1H); 6.04 (m, 1H); 6.95 (d, J=8 Hz, 1H); 7.19 (dd, J=8 Hz, 2 Hz, 1H); 7.3 8 (d, J=2 Hz, 1H).

Reference Example 25

4-Methylthiazol-5-ylsulphonamide

2-Acetylamino-4-methylthiazoly-5-ylsulfonamide (100 mg) was dissolved in hydrazinehydrate (1.1 ml)and stirredatambient temperature for 2 hours. Water (20 ml) was added then the mixture extracted with ethyl acetate(5×50 ml). The combined organics were evaporated, azeotroped with toluene and purified by MPLC (silica , 5% ethanol/ dichloromethane) to give 2-amino-4-methylthiazoly-5-ylsulfonamide as a waxy solid (170 mg, 46%).

MS: 192 (M+H)$^+$; NMR (MHz, DMSO-$d_6$) δ: 2.3 (s, 3H); 7.25 (brs, 2H); 7.4 (brs, 2H).

A solution of give 2-amino-4-methylthiazoly-5-ylsulfonamide (150 mg, 0.78 mmol) in THF (5.5 ml) was added to a solution of amyl nitrite (0.23 ml, 1.56 mmol) heated at reflux dropwise over 30 minutes. The mixture was heated at reflux for a further 3 hours after which a further portion of amyl nitrite (0.5 ml) was added and the reaction mixture heated for a further 16 hours. The mixture was allowed to cooled, evaporated to dryness and the residue purified by MPLC (5–10% ethanol/dichloromethane) to give the title compound as a light brown waxy solid. (40 mg, 29%).

MS: 179 (M+H)$^+$; NMR (MHz, DMSO-$d_6$) δ: 2.6 (s, 3H); 7.8 (d, 2H); 9.1 (brs, 1H).

Reference Example 26

6-[N-(5-Bromo-2-(2-methylprop-2-en-1-yloxy) benzyl)-N-ethylamino]pyridazine-3-carbohydrazide Butyl 6-[N-(5-bromo-2-(2-methylprop-2-en-1-yloxy) benzyl)-N-ethylamino]pyridazine-3-carboxylate (reference example 4) (4.3 g, 9.3 mmol) was dissolved in ethanol (170ml) with hydrazine hydrate (17 ml, 330 mmol) and heated at reflux for 16 hours. The solvent was removed in vacuo, and the residue treated with ethyl acetate/water (200 ml of each). The organic phase separated off and the aqueous phase reextracted with ethyl acetate (2×200 ml). The combined organic phases were dried (MgSO$_4$) and concentrated in vacuo to give the title compound as an oil which crystallised on standing (3.66 g, 94%).

MS: 420 (M+H)$^+$, 442 (M+Na)$^+$; NMR (MHz, DMSO-$d_6$) δ: 1.31 (t, 3H); 1.56 (s, 3H); 3.67 (q, 2H); 4.85 (brs, 2H); 4.52 (s, 2H); 4.82 (s, 2H); 4.97 (s, 1H); 5.08 (s, 1H); 6.97 (d, 1H); 7.1 (m, 2H); 7.37 (dd, 1H); 7.77 (d, 1H); 9.8 (s, 1H).

Reference Example 27

Ethyl 6-[N-(5-bromo-2-hydroxybenzyl)-N-ethylamino]pyridazine-3-carboxylite

The 6-[N-(5-bromo-2-hydroxybenzyl)-N-ethylamino] pyridazine-3-carboxylic acid (example 8) (6.5 g) was suspended in ethanol (30 ml) and treated cautiously with concentrated sulphuric acid (1.5 ml). The reaction was heated to reflux overnight, then the organic solvent was evaporated. The residue was partitioned between ethyl acetate/water and the organic phase was dried over (MgSO$_4$) and evaporated to give the title compound as a brown solid (5.86 g).

M.S. (ESP)$^+$: 380 (M+H)$^+$; NMR (200 MHz, DMSO-$d_6$) δ: 1.16(t, 3H); 1.33(t, 3H); 3.7(q, 2H); 4.35 (q, 2H); 4.76(s,

2H); 6.8(d, 1H); 7.1(m, 2H); 7.26(dd, 1H); 7.83 (d, 1H); 10.19(br s, 1H).

Reference Example 28

Butyl 6-[N-(5-bromo-2-(but-2-enyloxy)benzyl)-N-ethylamino]pyridazine-3-carboxylate The title compound was preferred from butyl 6-[N-(5-bromo-2-hydroxybenzyl)-N-ethylamino]pyridazine-3-carboxylate using a similar method to that of reference example 9 (E.Z mixture of 2:1).

NMR (200 MHz, DMSO-$d_6$) δ 0.94(t, 3H); 1.15(t, 3H); 1.4(m, 2H); 1.7(bm, 5H); 3.69 (q, 2H); 4.3(t, 2H); 4.52 and 4.66 (2d, together 2H); 4.81 (s, 2H); 5.7e(m, 2H); 7.0(d, 1H); 7.07(d, 1H); 7.13(d, 1H); 7.4(dd, 1H); 7.82(d, 1H).

Reference Example 29

Ethyl 6-(N-[5-Bromo-2-(2-methylprop-2-en-1-yloxy)benzyl)I-N-ethylamino)pyridazine-3-carboxylate A mixture of 6-[N-(5-bromo-2-(2-methylprop-2-en-1-yloxy)benzyl)-N-ethylamino]pyridazine-3-carboxylic acid (example 2, compound 15) (2.1 g, 5.2 mmol) and carbonyl di-imidazole (1.0 g, 5.9 mmol) was stirred in dry THF (25 ml) under argon at 40–50° C. for 1 hour. The resulting solution was added to the magnesium enolate prepared from a mixture of potassium ethyl malonate (1.1 g, 6.5 mmol), triethylamine (1.2 ml, 8.6 mmol) and anhydrous magnesium chloride (0.7 g, 7.4 mmol) in acetonitrile (40 ml) which had been stirred at 20–25° C. under argon for 2 hours.

The mixture was stirred at 25° C. for 16 hours, refluxed for 30 minutes, cooled and then evaporated at reduced pressure. The residue was partitioned between dichloromethane (100 ml) and 2N HCl (100 ml). The organic layer was separated, dried over anhydrous magnesium sulphate and filtered through a silica pad, rinsing through with ether. The combined filtrates were evaporated to give the title compound as a colourless gum (1.2 g).

What is claimed is:

1. Any compound according to formula Ia:

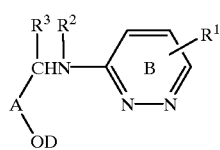

Ia wherein:

A is selected from phenyl and naphthyl, where A is either unsubstituted, mono-, or di-substituted with halo;

provided that the —CH($R^3$)N($R^2$)-linking group and the —OD group are positioned in a 1,2 relationship on A and the ring atom of A in the 3-position is not substituted;

ring B is either unsubstituted or non-substituted with —$SO_p$($C_1$–$C_6$)alkyl, carbamoyl, ($C_1$–$C_4$)alkylcarbamoyl, di(($C_1$–$C_4$)alkyl)carbamoyl, and G where G is selected from halo, trifluoromethyl, nitro, hydroxy, ($C_1$–$C_6$)alkoxy, ($C_1$–$C_6$)alkyl, amino, ($C_1$–$C_4$)alkylamino, di(($C_1$–$C_4$)alkyl)amino and cyano;

$R^1$ is positioned on ring B in a 1,4 relationship with the —CH($R^3$)N($R^2$)-linking group;

$R^1$ is selected from carboxy, carbamoyl, tetrazolyl, —CONR$^a$R$^{a1}$ where R$^a$ is hydrogen or ($C_1$–$C_6$)alkyl and R$^{a1}$ is ($C_1$–$C_6$)alkyl or ($C_1$–$C_6$)alkyl substituted by hydroxy, ($C_2$–$C_6$)alkenyl 1-morpholinyl, 1-piperidinyl, 1-pyrrolidinyl, or pyridyl($C_1$–$C_3$)akyl, $R^2$ is hydrogen, ($C_1$–$C_6$)alkyl, ($C_1$–$C_6$)alkyl substituted by hydroxy, cyano or trifluoromethyl, $CH_2$-($C_1$–$C_5$) alkenyl, $CH_2$-($C_1$–$C_5$)alkynyl, phenyl($C_1$–$C_3$)alkyl or pyridyl($C_1$–$C_3$)alkyl;

$R^1$ is hydrogen, methyl or ethyl;

D is hydrogen, a 5–7 membered carbocyclic ring having one double bond, a 5–7 membered carbocyclic ring having one double bond mono-substituted with L where L is selected from ($C_1$–$C_4$)alkyl, ($C_2$–$C_4$) alkenyl, ($C_2$–$C_4$)alkynyl halo, hydroxy, amino, ($C_1$–$C_4$) alkylamino, di-(($C_1$–$C_4$)alkyl)amino, cyano, trifluoromethyl, oxo, ($C_1$–$C_4$)alkanoyl, (carboxy and carbamoyl, ($C_1$–$C_3$)alkyl substituted with a 5–7 membered carbocyclic ring having one double bond, or a 5–7 membered carbocyclic ring having one double bond mono-substituted with L or ($CH_2$)$_n$CH($R^4$)C($R^5$)=C($R^6$)$R^7$ where $R^4$ is hydrogen, methyl or ethyl, $R^5$ is methyl or M where M is hydrogen, bromo, chloro, fluoro or trifluoromethyl, $R^6$ and $R^7$ are ($C_1$–$C_4$)alkyl or M, and n is 0 or 1;

or compounds that are N-oxides of N—$R^2$, where chemically possible;

or a pharmaceutically-acceptable salt of any foregoing compound.

2. Any compound according to claim 1, wherein $R^1$ is selected from carboxy, tetrazole and —CONHR$^{a1}$ where R$^{a1}$ is pyridylmethyl, ($C_1$–$C_4$)alkyl, ($C_1$–$C_4$)alkyl substituted by hydroxy, or $R^1$ is —CONHSO$_2$R$^b$ where R$^b$ is ($C_1$–$C_4$)alkyl, 3,5-dimethylisoxazol-4-yl or 5-acetamido-1,3,4-thiadiazol-2-yl.

3. Any compound according to claim 1, wherein A is phenyl.

4. Any compound according to claim 1, wherein $R^3$ is hydrogen.

5. Any compound according to claim 1, wherein $R^2$ is hydrogen, methyl, ethyl or propyl.

6. Any compound according to claim 1, wherein D is hydrogen.

7. Any compound according to claim 1, wherein D is a 5- or 6-membered carbocyclic ring having one double bond; a methyl-substituted 5- or 6-membered carbocyclic ring having one double bond; methyl; methyl substituted by a 5- or 6-membered carbocyclic ring having one double bond, or —$CH_2$C($R^5$)=C($R^6$)$R^7$ where $R^5$, $R^6$ and $R^7$ are as defined in claim 1.

8. A pharmaceutical composition comprising any compound according to claim 1 and at least one pharmaceutically-acceptable carrier.

9. A method of relieving pain in a patient suffering therefrom, said method comprising administering an effective amount of at least one compound according to claim 1.

10. A compound selected from:

6-[N-(5-bromo-2-(2-methylprop-2-en-1-yloxy)benzyl)-N-ethylamino]pyridazin-3-ylcarboxylic acid, 6-[N-(5-bromo-2-(prop-2-en-1-yloxy)benzyl)-N-ethylamino]pyridazin-3-ylcarboxylic acid, 6-[N-(5-bromo-2-(but-2-en-1-yloxy)benzyl)-N-ethylamino]pyridazin-3-ylcarboxylic acid, 6-[N-(5-bromo-2-(2-chloroprop-2-en-1-yloxy)benzyl)-N-ethylamino]pyridazin-3-ylcarboxylic acid, 6-[N-(5-bromo-2-hydroxybenzyl)-N-ethylamino]pyridazin-3-ylcarboxylic acid, 5-[6-(N-(5-bromo-2-(2-methylprop-2-en-1-yloxy)benzyl)-N-ethylamino)pyridazinyl]-tetrazole, 5-[6-(N-(5-bromo-2-(cyclohex-2-enyloxy)benzyl)-N-ethylamino]pyridazin-3-yl]tetrazole, N-propanesulphonyl-6-[N-(5-bromo-2-(2-methylprop-2-en-1-yloxy)benzyl)-N-ethylamino]pyridazin-3-ylcarboxamide, N-benzenesulphonyl-6-[N-(5-bromo-2-(2-methylprop-2-en-1-yloxy)benzyl)-N-ethylamino]pyridazin-3-ylcarboxamide, N-benzenesulphonyl-6-[N-(5-bromo-2-(2-chloroprop-2-en-1-yloxy)benzyl)-N-ethylamino]pyridazin-3-ylcarboxamide, N-propanesulphonyl-6-[N-(5-bromo-2-(2-chloroprop-2-en-1-yloxy)benzyl)-N-ethylamino]pyridazin-3-ylcarboxamide, N-propanesulphonyl-6-[N-(5-bromo-2-(cyclohexen-3-yloxy)benzyl)-N-ethylamino]pyridazin-3-ylcarboxamide, N-benzenesulphonyl-6-[N-(5-bromo-2-(cyclohexen-3-yloxy)benzyl)-N-ethylamino]pyridazin-3-ylcarboxamide, N-(3,5-dimethylisoxazol-4-yisulphonyl)-6-[N-(5-bromo-2-(prop-2-en-1-yloxy)benzyl)-N-ethylarnino]pyridazin-3-ylcarboxamide, N-(5-acetylamino-1,3,4-thiadiazol-2-ylsulphonyl)-6-[N-(5-bromo-2-(prop-2-en-1-yloxy)benzyl)-N-ethylamino]pyridazin-3-ylcarboxamide, 6-[N-(5-bromo-2-(2-methylprop-2-en-1-yloxy)benzyl)-N-ethylamino]pyridazin-3-ylcarboxylic acid, 6-[N-(5-bromo-2-(2-chloroprop-2-en-1-yloxy)benzyl)-N-ethylamino]pyridazin-3-ylcarboxylic acid, 6-[N-(5-bromo-2-(cyclohexen-3-yloxy)benzyl)-N-ethylamino]pyridazin-3-ylcarboxylic acid, N-(3,5-dimethylisoxazol-4-ylsulphonyl)-6-[N-(5-bromo-2-(2-methylprop-2-en-1-yloxy)benzyl)-N-ethylamino]pyridazin-3-ylcarboxamide, 6-[N-(5-chloro-2-(2-methylprop-2-en-1-yloxy)benzyl)-N-ethylamino]pyridazin-3-ylcarboxamide, 6-[N-(5-chloro-2-(2-methylprop-2-en-1-yloxy)benzyl)-N-ethylamino]pyridazin-3-ylcarboxylic acid, N-(2-(pyrrolidino)ethanesulphonyl)-6-[N-(5-chloro-2-(2-methylprop-2-en-1-yloxy)benzyl)N-ethylamino]pyridazin-3-ylcarboxamide, N-(2-(morpholino)ethanesulphonyl)-6-[N-(5-chloro-2-(2-methylprop-2-en-1-yloxy)benzyl)-N-ethylamino]pyridazin-3-ylcarboxamide, 6-[N-(5-fluoro-2-(2-methylprop-2-en-1-yloxy)benzyl)-N-ethylamino]pyridazin-3-ylcarboxylic acid, 6-[N-(5-chloro-2-(cyclohexen-3-yloxy)benzyl)-N-ethylamino]pyridazin-3-ylcarboxylic acid, N-(3,5-dimethylisoxazol-4-ylsulphonyl)-6-[N-(5-chloro-2-(cyclohexen-3-yloxy)benzyl)-N-ethylamino]pyridazin-3-ylcarboxamide, 5-[6-(N-[5-chloro-2-(2-methylprop-2-en-1-yloxy)benzyl]-N-ethylamino)pyridazin-3-yl]tetrazole, N-(3,5-dimethylisoxazol-4-ylsulphonyl )-6-[N-(5-chloro-2-(2-methylprop-2-en-1-yloxy)henzyl)-N-ethylamino]pyridazin-3-ylcarboxamide, N-(trifluoromethanesulphonyl)-6-[N-(5-chloro-2-(2-methylprop-2-en-1-yloxy)benzyl)-N-ethylamino]pyridazin-3-ylcarboxamide, N-(2-carboxyphenyl)-6-[N-(5-chloro-2-(2-methylprop-2-en-1-yloxy)benzyl)-N-ethylamino]pyridazin-3-ylcarboxamide, N-(1-carboxyethyl)-6-[N-(5-chloro-2-(2-methylprop-2-en-1-yloxy)benzyl)-N-ethylamino]pyridazin-3-ylcarboxamide, N-(α-carboxybenzyl)-6-[N-(5-chloro-2-(2-methylprop-2-en-1-yloxy)benzyl)-N-ethylamino]pyridazin-3-ylcarboxamide, N-(3,5-dimethylisoxazol-4-ylsulphonyl)-6-[N-(5-chloro-2-allyloxybenzyl )-N-ethylamino]pyridazin-3-ylcarboxamide, 6-[N-(5-chloro-2-allyloxybenzyl)-N-ethylamino]pyridazin-3-ylcarboxamide, 6-[N-(5-chloro-2-allyloxybenzyl)-N-ethylamino]pyridazin-3-ylcarboxylic acid, N-(4-methylthiazol-5-ylsulphonyl)-6-[N-(5-bromo-2-(2-methylprop-2-en-1-yloxy)benzyl)-N-ethylamino]pyridazin-3-ylcarboxamide, 5-[6-(N-[5-bromo-2-(2-methylprop-2-en-1-yloxy)benzyl]-N-ethylamino)pyridazin-3-yl]-2-thioxo-2,3-dihydro-1,3,4-oxadiazole, 2-[6-(N-[5-bromo-2-(2-methylprop-2-en-1-yloxy)benzyl]-N-ethylamino)pyridazin-3-yl]-1,3,4-oxadiazole, 6-[N-(5-chloro-2-(2-methylprop-2-en-1-yloxy)benzyl)-N-ethylamino]pyridazin-3-ylsulphonamide, and 5-[6-(N-(5-bromo-2-(2-methylprop-2-en-1-yloxy)benzyl)-N-ethylamino)pyridazin-3-yl]-3-hydroxy-2-methylpyrazole; or or a pharmaceutically-acceptable salt of any of foregoing compound.

11. Any compound according to claim 1, wherein $R^2$ is hydrogen, methyl, ethyl or propyl.

* * * * *